US008519146B2

(12) United States Patent
Youngs et al.

(10) Patent No.: US 8,519,146 B2
(45) Date of Patent: Aug. 27, 2013

(54) METAL COMPLEXES OF N-HETEROCYCLIC CARBENES AS ANTIBIOTICS

(75) Inventors: Wiley J. Youngs, Akron, OH (US);
Claire A. Tessier, Akron, OH (US);
Jered Garrison, Columbia, MO (US);
Carol Quezada, Canal Fulton, OH (US);
Abdulkareem Melaiye, Akron, OH (US); Matthew Panzner, Akron, OH (US); Semih Durmus, Akron, OH (US)

(73) Assignee: The University of Akron, Akron, OH (US)

( * ) Notice: Subject to any disclaimer, the term of this patent is extended or adjusted under 35 U.S.C. 154(b) by 1160 days.

(21) Appl. No.: 11/482,410

(22) Filed: Jul. 7, 2006

(65) Prior Publication Data
US 2007/0021401 A1    Jan. 25, 2007

Related U.S. Application Data

(63) Continuation-in-part of application No. 10/569,563, filed as application No. PCT/US2004/029285 on Sep. 7, 2004, now abandoned.

(51) Int. Cl.
*C07F 15/00* (2006.01)
*C07F 1/00* (2006.01)

(52) U.S. Cl.
USPC .......................................... 548/103; 544/225

(58) Field of Classification Search
USPC ........................................... 544/225; 548/103
See application file for complete search history.

(56) References Cited

U.S. PATENT DOCUMENTS

| | | | |
|---|---|---|---|
| 4,677,143 A * | 6/1987 | Laurin et al. ................... | 424/618 |
| 5,262,532 A | 11/1993 | Tweedle et al. | |
| 5,405,957 A | 4/1995 | Tang et al. | |
| 5,703,269 A | 12/1997 | Herrmann et al. | |
| 5,728,839 A | 3/1998 | Herrmann et al. | |
| 5,994,365 A | 11/1999 | Zaworotko et al. | |
| 6,025,496 A | 2/2000 | Herrmann et al. | |
| 6,288,197 B1 | 9/2001 | Youngs et al. | |
| 6,316,380 B1 | 11/2001 | Nolan et al. | |
| 6,492,525 B1 | 12/2002 | Bertrand et al. | |
| 6,794,327 B2 | 9/2004 | Youngs et al. | |
| 6,919,448 B2 | 7/2005 | Youngs et al. | |
| 2003/0190370 A1* | 10/2003 | Kim et al. ...................... | 424/618 |

FOREIGN PATENT DOCUMENTS

| WO | WO02085385 | * | 10/2002 |
|---|---|---|---|
| WO | WO2005/023760 | * | 3/2005 |

OTHER PUBLICATIONS

Melaiye et al., Formation of water-soluble pincer silver (I)—carbene complexes: a novel antimicrobial agent. J. Med. Chem. 47, 973-77 (published online Jan. 14, 2004).*

Kascatan-Nebioglu et al., Synthesis and structural characterization of N-heterocyclic carbene complexes of silver (I) and rhodium (I) from caffeine. Organomet. 23, 1928-1931 (published online Mar. 19, 2004).*
Ramnial et al. A Monomeric Imidazol-2-ylidene Silver(I) Chloride Complex: Synthesis, Structure, and Solid State 109Ag and 13C CP/MAS NMR Characterization. Inorg. Chem. 42, 1391-93 (2003).*
Richard S. Simons et al.; "Formation of N-Heterocyclic Complexes of Rhodium and Palladium from a Pincer Silver(I) Carbene Complex;" Organometallics; vol. 22, No. 9; 2003; pp. 1979 to 1982.
Jered Garrison et al.; "Synthesis and structural characterization of a silver complex of a mixed-donor N-heterocyclic carbene linked cyclophane;" Chemical Communications, No. 18; Sep. 21, 2001; pp. 1780 to 1781.
Andreas A. Danopoulos et al.; "Chelating and 'pincer' dicarbene complexes of palladium; synthesis and structural studies;" Journal of the Chemical Society, Dalton Transactions; 2003; pp. 1009 to 1015.
Ermitas Alcalde et al.; "Open-Chain Dications and Betaines with Imidazolium Molecular Motifs: Synthesis and Structural Aspects;" European Journal of Organic Chemistry; vol. 2002; Issue 7; pp. 1221 to 1231.
David J. Nielsen et al.; "A pyridine bridged dicarbene ligand and its silver(I) and palladium(II) complexes; synthesis, structures, and catalytic applications;" Inorganica Chimica Acta 327; 2007; pp. 116 to 125.
European Search Report for European Patent Application No. 04788633, dated Nov. 6, 2007.
Simons, Richard S., et al., "Formation of N-Heterocyclic Complexes of Rhodium and Palladium from a Pincer Silver (1) Carbene Complex", Organometallics, ACS, Washington, DC, vol. 22, No. 22. (2003).

(Continued)

*Primary Examiner* — Barbara P Badio
*Assistant Examiner* — Sara E Townsley
(74) *Attorney, Agent, or Firm* — REnner Kenner Greive Bobak Taylor Weber

(57) ABSTRACT

A method for inhibiting microbial growth comprises administering an effective amount of a silver complex of a N-heterocyclic amine. A method for treating cancer cells or a method for imaging one or more tissues of a patient includes administering an effective amount of a complex of a N-heterocyclic amine and a radioactive metal. A method for treating urinary tract infections utilizing silver complexes of N-heterocyclic carbenes. N-heterocyclic carbenes of the present invention may be represented by the formula

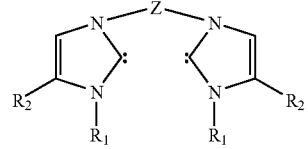

wherein Z is a heterocyclic group, and $R_1$ and $R_2$ are, independently or in combination, hydrogen or a $C_1$-$C_{12}$ organic group selected from the group consisting of alkyl, cycloalkyl, alkenyl, cycloalkenyl, alkynyl, aryl, arylalkyl, alkylaryl, heterocyclic, and alkoxy groups and substituted derivatives thereof.

2 Claims, 16 Drawing Sheets

(56) References Cited

OTHER PUBLICATIONS

Garrison, J.C., et al., "Synthesis and Structural Characterization of a Silver Complex of a Mixed-Donor N-Heterocyclic Carbene Linked Cyclophane", Chemical Communications 21, Sep. 2001, United Kingdom No. 18.

Danopoulos, A.A., et al: "Chelating and Pincer: Dicarbene Complexes of Palladium; Synthesis and Structural Studies", Journal of the Chemical Society, Dalton Transactions, Chemical Society, Letchworth, GB Jan. 30, 2003.

Aldalde E., et al., "Open-Chain Dications and Betaines with Imidazolium Molecular Motifs: Synthesis and Structural Aspects", Chemistry—A European Journal, VCH Publishers, US, 2002, pp. 1221-1231.

Nielsen, et al., "A Pyridine Bridged Dicarbene Ligand and its Silver(a) and Palladium(II) Complexes: Synthesis, Structures, and Catalytic Applications", Inorganica Chimica ACTA, X, XX, vol. 327, 2002 pp. 116-125.

* cited by examiner

METAL COMPLEXES OF N-HETEROCYCLIC CARBENES AS ANTIBIOTICS

This is a continuation-in-part of International Application PCT/US2004/029285, with an international filing date of Sep. 7, 2004. The application entered the national stage in the United States on Feb. 27, 2006 as application Ser. No. 10/569,563.

STATEMENT REGARDING FEDERALLY SPONSORED RESEARCH OR DEVELOPMENT

This invention was made with government support under grants, Award Number NIH R15 CA 96739-01; and Award Number NSF CHE-0116041. The government may have certain rights to the invention.

BACKGROUND OF THE INVENTION

This invention relates to metal-containing, therapeutic, antimicrobial, and antifungal compounds. More particularly, this invention relates to metal complexes of N-heterocyclic carbenes and their use as antimicrobial agents, antifungal agents and radiopharmaceutical compositions.

Silver has long been used for its antimicrobial properties. This usage predates the scientific or medical understanding of its mechanism. For example, the ancient Greeks and Romans used silver coins to maintain the purity of water. Today silver is still used for this same purpose by NASA on its space shuttles. Treatment of a variety of medical conditions using silver nitrate was implemented before 1800. A 1% silver nitrate solution is still widely used today after delivery in infants to prevent gonorrheal ophthalmia. Since at least the later part of the nineteenth century, silver has been applied in a variety of different forms to treat and prevent numerous types of bacteria related afflictions.

Other treatments, such as the application of silver foil to post surgical wounds to prevent infection survived as a medical practice into the 1980's in Europe, and silver nitrate is still used as a topical antimicrobial agent. In the 1960's the very successful burn treatment silver complex, silver sulfadiazine, shown in formula 1 below, was developed. Commercially known as Silvadene® Cream 1%, this complex has remained one of the most effective treatments for preventing infection of second and third degree burns. Silver sulfadiazine has been shown to have good antimicrobial properties against a number of gram-positive and gram-negative bacteria. It is believed that the slow release of silver at the area of the superficial wound is responsible for the process of healing. Studies on surgically wounded rats have shown the effectiveness of both silver nitrate and silver sulfadiazine to aid in the healing process. By using these common silver antimicrobial agents, inflammation and granulation of wounds were reduced, although the complete mechanism for these phenomena is not understood.

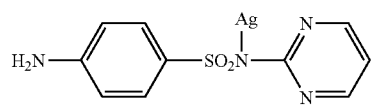

1

Recently developed silver-coating techniques have lead to the creation of a burn wound dressing called Acticoat. The purpose of this dressing is to avoid adhesion to wounds while providing a barrier against infection. Some clinical trials have also demonstrated the ease of removal of the dressing in contrast to conventional wound dressings treated with silver nitrate. Acticoat has shown an increase in antibacterial function over both silver nitrate and silver sulfadiazine. Acticoat is made up of nanocrystalline silver particles. Antibiotic-resistant strains have developed rarely to both silver nitrate and silver sulfadiazine but not to nanocrystalline silver. The broader range of activity of nanocrystalline silver is apparently due to the release of both silver cations and uncharged silver species. Due to the continuing emergence of antibiotic resistant strains of infectious agents, a need exists for novel antibiotics.

Metal compounds have also played a significant role in other therapeutic applications. One example of the usefulness of the metals can be seen in the field of radiopharmaceuticals. The use of radiation therapy to destroy tumor cells is well known, but tumors can reappear after therapy. Hypoxic cells within the tumor are 2.5 to 3 times more resistant to X-ray radiation than other tumor cells. For this reason, these cells are more likely to survive radiation therapy or chemotherapy and lead to the reappearance of the tumor. Targeting of radionuclides to hypoxic cells will serve as a method to visualize them.

Complexes of γ-ray emitters such as $^{99}$Tc are extremely useful as imaging agents, and therapeutic radiopharmaceuticals like $^{89}$Sr, $^{153}$Sm, $^{186}$Re and $^{166}$Ho are important in the treatment of bone tumors. Rh-105 emits a gamma ray of 319 keV (19%) that would allow in vivo tracking and dosimetry calculations. Many more radioactive nuclei can be harnessed by using the entire periodic table to construct diagnostic or therapeutic agents.

Urinary tract infections (UTIs) represent the second most common infectious disease in the United States and are associated with substantial morbidity and medical cost. These infections, including cystitis and pyelonephritis, are most commonly caused by uropathogenic *Escherichia coli* (UPEC). Patients with neurogenic bladder, indwelling urinary catheters, or vesicoureteral reflux, as well as otherwise healthy women, experience recurrences; repeated infections of the urinary tract can lead to renal scarring and chronic kidney disease (CKD). Current preventive and therapeutic strategies fail to address the problem of recurrent UTIs. Recent work in the murine cystitis model has unveiled new paradigms regarding the pathogenesis of UTI. Long thought to be strictly extracellular pathogens, UPEC have been shown to invade superficial epithelial cells lining the bladder and to establish large collections, termed intracellular bacterial communities (IBCs), within these cells. From there, UPEC form a quiescent reservoir within bladder tissue that is sequestered from host defenses, resists antibiotic therapies, and can serve as a nidus for recurrence.

The rapid rise in antimicrobial resistance rates among pathogenic strains renders treatment and prophylactic regimens for UTI increasingly difficult. For this reason, it is desired to interrogate the utility of silver carbenes as novel antimicrobials within the urinary tract. The antimicrobial properties of silver have been recognized for centuries, and there is recent resurgence of interest in this metal as a biocide. Though silver-impregnated urinary catheters have reduced the incidence of UTI in certain populations (e.g., patients with indwelling catheters), novel strategies are needed to prevent recurrent UTI in other patients (e.g., healthy women and patients with functional and anatomic abnormalities of the urinary tract). Organometallic complexes of silver with N-heterocyclic carbenes (NHCs), have been designed and synthesized. The primary advantage of these silver carbenes (SCs) over existing silver compounds is their stability and water solubility.

The usefulness of complexes of radioactive metals is highly dependent on the nature of the chelating ligand. A successful metal drug must both target a specific tissue or organ as well as rapidly clear from other tissues. In addition, for both imaging and tumor treatment, the target organ or tissue must have optimal exposure to the radiopharmaceutical. Therefore, there is a need for novel ligand systems designed to bind radioactive metals.

BRIEF DESCRIPTION OF THE FIGURES

FIG. 1a is a thermal ellipsoid plot of the cationic portions of the water soluble silver dimers shown in formula 9a.

FIG. 4 is a thermal ellipsoid plot of the bromide salt shown as formula 20a.

FIG. 26a details as-spun fiber and 26b details silver particles formed by exposing the as-spun fiber to water.

SUMMARY OF THE INVENTION

Figure 1A:
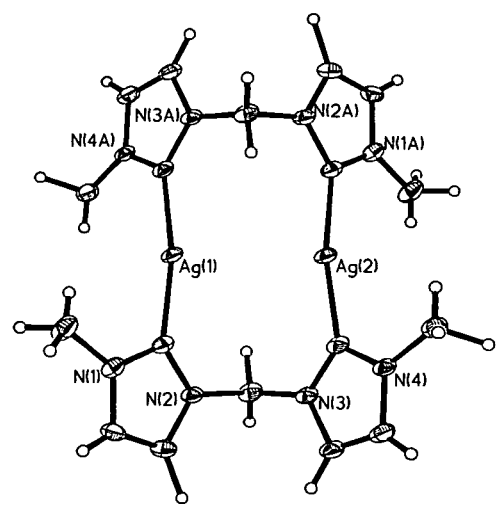

While metal complexes of some N-heterocyclic carbenes have been previously known, it has not been recognized that silver complexes of N-heterocyclic carbenes will act as antimicrobial agents. It has likewise not been recognized that complexes of N-heterocyclic carbenes and radioactive metals may be used as radiopharmaceuticals. Strongly chelating ligands, such as the pincer N-heterocyclic carbenes, described herein, can provide an alternate, more advantageous route for the generation of radiopharmaceutical complexes.

It is, therefore, an aspect of the present invention to provide a method for treating urinary tract infections comprising the step of administering an effective amount of a silver complex of an N-heterocyclic carbene.

Another aspect of the invention are the N-heterocyclic carbines represented by the formula

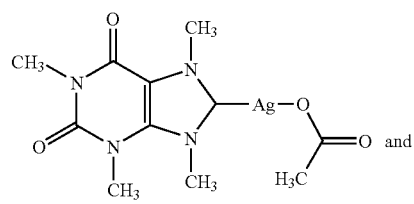 and

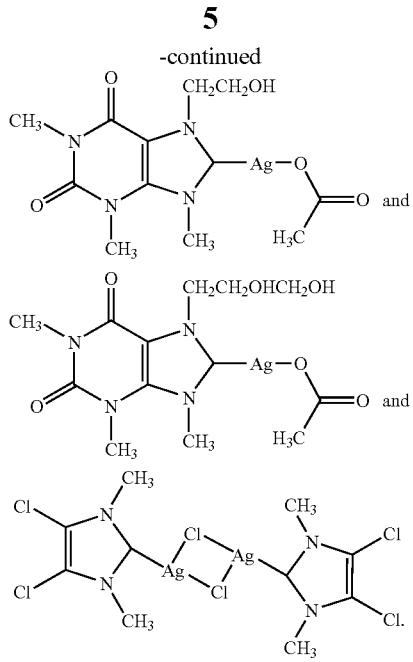

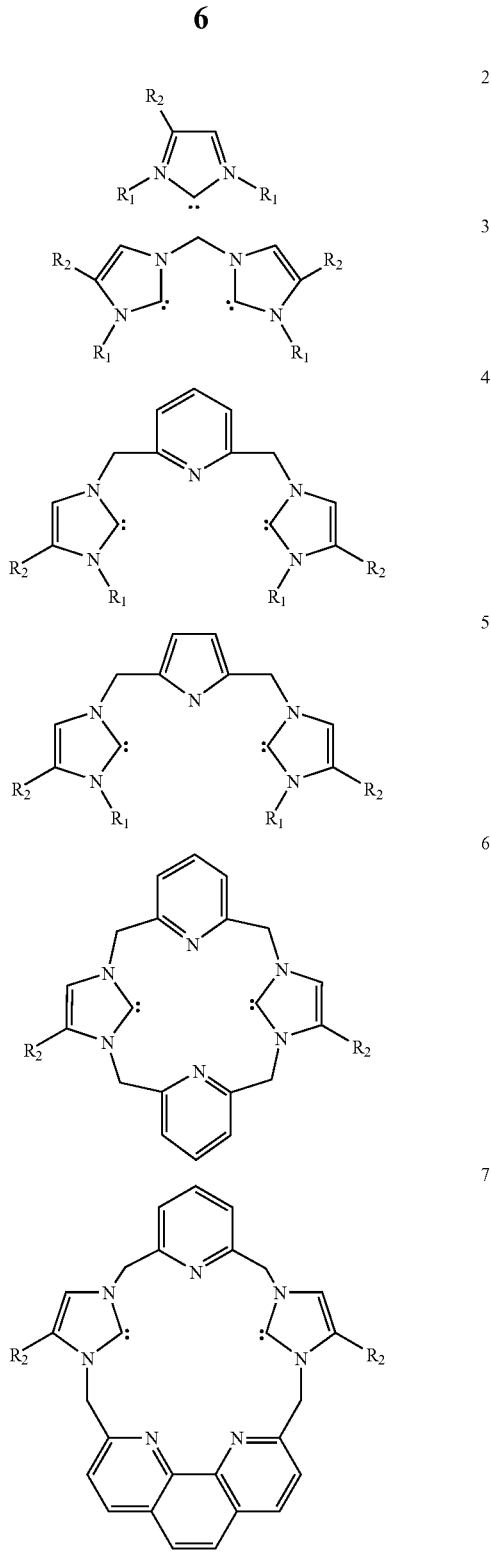

DETAILED DESCRIPTION OF THE INVENTION

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention pertains.

The present invention includes a metal complex of a N-heterocyclic carbene, its method of manufacture, and methods of use. Several general types of N-heterocyclic carbene ligands may be used as ligands for a metal such as silver. These include monodentate carbenes, such as those represented by formula 2, bidentate carbenes such as those represented by formulae 3-5, and bidentate macrocyclic carbenes such as those represented by formulae 6 and 7. With the exception of monodentate carbenes, each of these ligand types has as their basic constituent two N-heterocyclic carbene units bridged by either methylene groups, as in formula 3, dimethylpyridine groups, as in formula 4 and dimethylpyrrole groups as in formula 5, or are parts of rings as in formulae 6 and 7. The water solubility, stability, charge and lipophilicity of silver complexes of these N-heterocyclic carbenes may be modified by changes in $R_1$ and $R_2$. Each $R_1$ and $R_2$, separately or in combination, may be selected from the group consisting of hydrogen, $C_1$-$C_{12}$ alkyl, $C_1$-$C_{12}$ substituted alkyl, $C_1$-$C_{12}$ cyclo alkyl, $C_1$-$C_{12}$ substituted cycloalkyl, $C_1$-$C_{12}$ alkenyl, $C_1$-$C_{12}$ cycloalkenyl, $C_1$-$C_{12}$ substituted cycloalkenyl, $C_1$-$C_{12}$ alkynyl, $C_1$-$C_{12}$ aryl, $C_1$-$C_{12}$ substituted aryl, $C_1$-$C_{12}$ arylalkyl, $C_1$-$C_{12}$ alkylaryl, $C_1$-$C_{12}$ heterocyclic, $C_1$-$C_{12}$ substituted heterocyclic and $C_1$-$C_{12}$ alkoxy. It is particularly desirable, for at least some pharmaceutical applications, for $R_1$ and $R_2$ to be selected such that the resulting metal/N-heterocyclic carbene complex is soluble and stable in an aqueous solution.

In one example, the N-heterocyclic carbene is a bidentate carbene represented by formula 4 or 5, where $R_1$ is a $C_1$-$C_6$ alkyl or $C_1$-$C_6$ hydroxyalkyl group, and $R_2$ is a hydrogen atom. In one particular example, the N-heterocyclic carbene is represented by formula 4 or 5, where $R_1$ is a $C_2$-$C_3$ hydroxyalkyl group, and $R_2$ is a hydrogen atom. In another example, the N-heterocyclic carbene is represented by formula 4 and each adjacent $R_1$ and $R_2$ together forms a substituted alkyl group.

As stated above, the present invention also provides novel N-heterocyclic carbenes represented by the formula

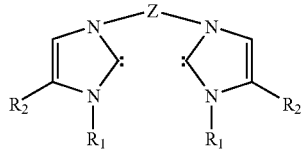

wherein Z is a heterocyclic group, and $R_1$ and $R_2$ are, independently or in combination, hydrogen or a $C_1$-$C_{12}$ organic group selected from the group consisting of alkyl, substituted alkyl, cyclo alkyl, substituted cycloalkyl, alkenyl, cycloalkenyl, substituted cycloalkenyl, alkynyl, aryl, substituted aryl, arylalkyl, alkylaryl, heterocyclic, substituted heterocyclic and alkoxy groups. In one example, Z is a pyridine or a pyrrole. In another example, Z is dimethylpyridine or dimethylpyrrole.

In general, imidazolium salts are the immediate precursors of N-heterocyclic carbenes. Several procedures may be used to convert imidazolium salts to the corresponding N-heterocyclic carbenes. N-Heterocyclic carbenes may be generated from imidazolium salts by deprotonation with bases such as KOtBu, KH, and NaH in solvents such as THF and liquid ammonia. Isolatable N-heterocyclic carbenes may replace two-electron donors (such as tetrahydrofuran, carbon monoxide, nitriles, phosphines, and pyridine) on a variety of transition metal complexes to give N-heterocyclic carbene transition metal complexes. However it has not always been practical to isolate the carbenes.

N-Heterocyclic carbene complexes may also be obtained by in situ generation of the N-heterocyclic carbene by deprotonation of the corresponding imidazolium salts in the presence of a suitable transition metal complex. Basic ligands on the metal complex, such as hydride, alkoxide, or acetate can deprotonate the imidazolium salt to form the N-heterocyclic carbene that readily binds to the vacant coordination site on a metal. For example $Pd(OAc)_2$ has been shown to react with a variety of imidazolium salts to form palladium-carbene complexes.

The imidazolium salt can also be treated with an inorganic or organic base to generate the carbene. The reaction of imidazolium salts with metals containing basic substituents has been shown to be quite useful for the synthesis of transition metal complexes of carbenes. The combination of the basic oxide, $Ag_2O$, with imidazolium salts may be used to generate silver-carbene complexes. The use of silver-carbene complexes as carbene transfer reagents has been used to provide carbene complexes of gold(I) and palladium(II). Silver-carbene complexes have been employed in this manner to provide complexes with Pd-carbene and Cu-carbene bonds. The formation of transition metal-carbene bonds, using carbene transfer reagents is favored in many situations because the reactions proceed under mild conditions and without the use of strong bases. For example, the condensation of 2 equivalents of n-butyl imidazole or methyl imidazole and 1 equivalent of diiodomethane in refluxing THF affords the imidazolium salts shown as formulae 8a or 8b in high yield. The combination of shown as formulae 8a or 8b with $Ag_2O$ in water forms the water soluble silver dimers 9a and 9b, respectively.

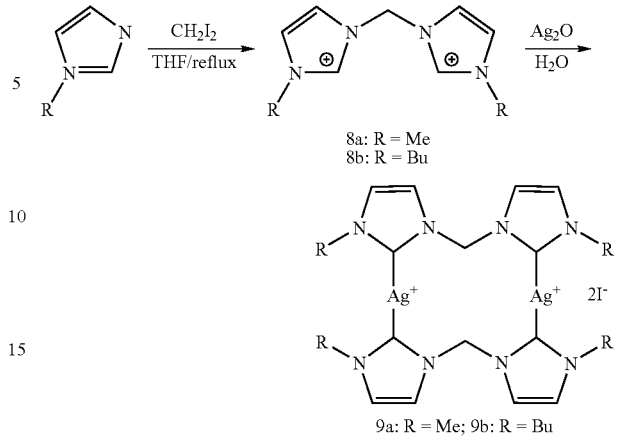

The combination of two equivalents of 1-iodoethanol (formula 12) with bisimidazol (formula 11) in refluxing butanol gives the water soluble diol shown as formula 13. This compound has been characterized by both NMR and X-ray crystallography.

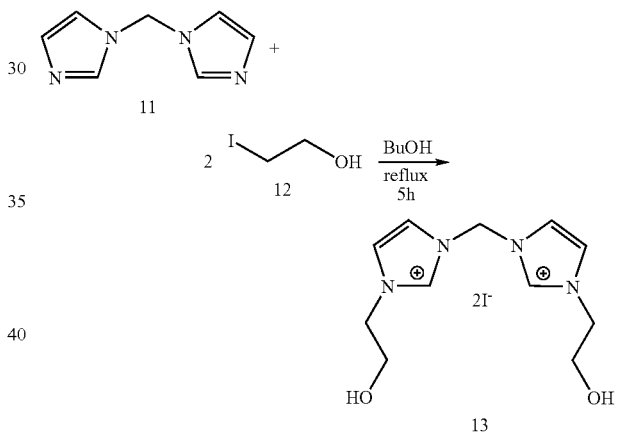

A similar reaction has been carried out using 1,2-dibromoethane (formula 14) with bisimidazol to form the carbene represented by formula 15. The alcohol groups of compound 13 and the bromides of compound 15 provide functionalized sites for the incorporation of solubilizing moieties.

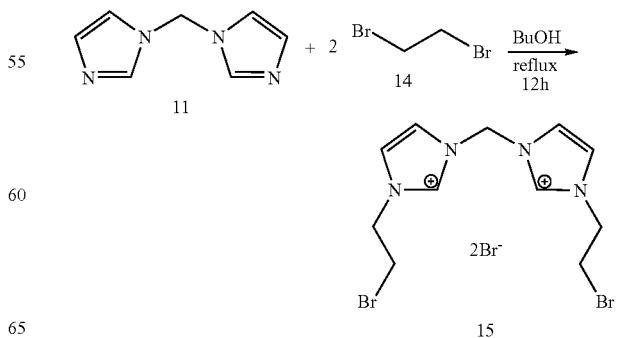

The pincer ligands 2,6-bis-(n-butylimidazoliummethyl)pyridine dihalide (compounds 16a and 16b) are easily obtained by the reaction of N-butyl imidazole with 2,6-bis(halogenmethyl)pyridine in a 2:1 molar ratio respectively. Ligand 16a readily reacts with Ag$_2$O in CH$_2$Cl$_2$ to yield the silver carbene complex 17. Complex 17 is stable in air and light.

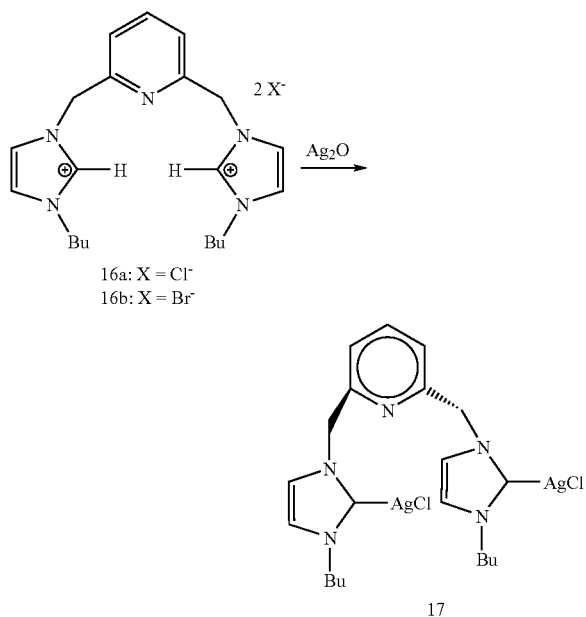

16a: X = Cl$^-$
16b: X = Br$^-$

17

A general synthesis of pincer N-heterocyclic carbenes with a pyridine as the bridging unit is presented below. The reaction of two equivalents of potassium imidazole with 2,6-bis(bromomethyl)pyridine resulted in compound 19 in 70% yield. The combination of the compound represented by formula 18 with 2-bromoethanol or 3-bromopropanol gave 19a and 19b, respectively. The combination of the Br$^-$ salt of 19a or 19b with an equimolar amount of Ag$_2$O gives the silver biscarbene polymers 20a and 20b, respectively. Compound 20a has been crystallographically characterized. The bromide salts represented by formulae 20a and 20b are very soluble and slowly decompose in water to give a silver mirror on the side of a flask containing either compound. 20a and its propanol analog 20b are effective antimicrobials. Derivatives of these complexes may be synthesized, using histidine as an example precursor as outlined below, to improve their antimicrobial properties.

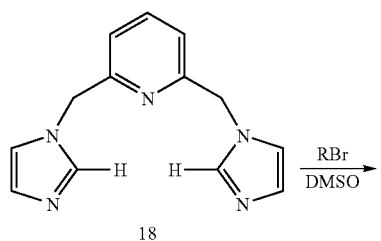

18

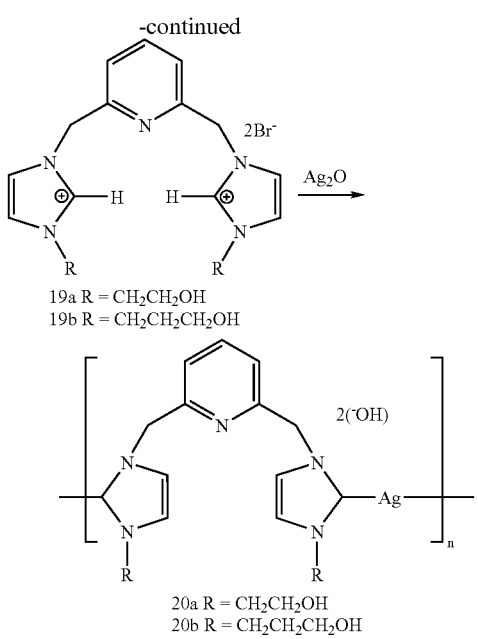

19a R = CH$_2$CH$_2$OH
19b R = CH$_2$CH$_2$CH$_2$OH

[structure with 2($^-$OH)]

20a R = CH$_2$CH$_2$OH
20b R = CH$_2$CH$_2$CH$_2$OH

The antimicrobial activity of water soluble silver (I) N-heterocyclic carbene 20a, in reference to silver nitrate, was investigated on yeast and fungi (*Candida albicans, Aspergillus niger, Mucorales, Saccharomyces cerevisiae*) using the LB broth dilutions technique, and bacteria (*E. coli, S. aureus, P. aeruginosa*) of clinical importance. The sensitivity test of the silver compounds using the Kirby-Bauer agar diffusion (filter paper disk) procedure, shows that silver (I) N-heterocyclic carbenes exhibit antimicrobial activity as effective as silver nitrate on all the bacteria by measuring the zone of growth inhibition using filter paper disks impregnated with solutions of the silver compound placed on a lawn of organism on an agar plate. Overnight cultures containing various concentrations of the silver compounds and bacteria or fungi were examined for growth. For each organism, the tube containing the minimum inhibitory concentration (MIC) for each silver compound was used to inoculate agar plates to confirm the absence of viable organisms in that culture. Compound 20a was effective on bacteria and fungi at lower concentrations, and had a longer period of silver activity than silver nitrate over the 7 day time course of the experiment. Toxicity studies with rats have shown that ligand 19a, the precursor to 20a and the material that forms on degradation of 20a, is of low toxicity and clears within two days through the kidneys as determined by Mass Spectroscopy of the urine.

Figure 5:
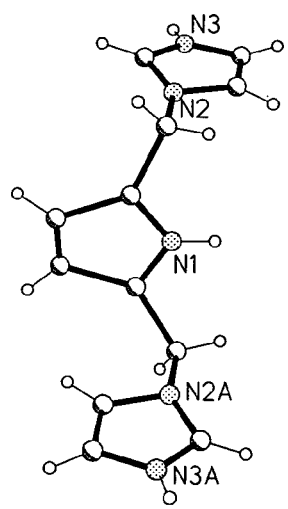
FIG. 5 is a thermal ellipsoid plot of the compound shown as formula 23.

The combination of two equivalents of potassium imidazole (formula 21) with 2,5-bis(trimethylaminomethyl)pyrrole diiodide (formula 22) in THF gives compound 23. Compound 23 has been crystallographically characterized and its thermal ellipsoid plot is shown as FIG. 5. Addition of two equivalents of butyl bromide to compound 23 gives compound 24 in high yield.

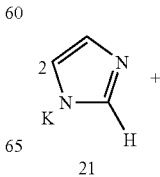

21

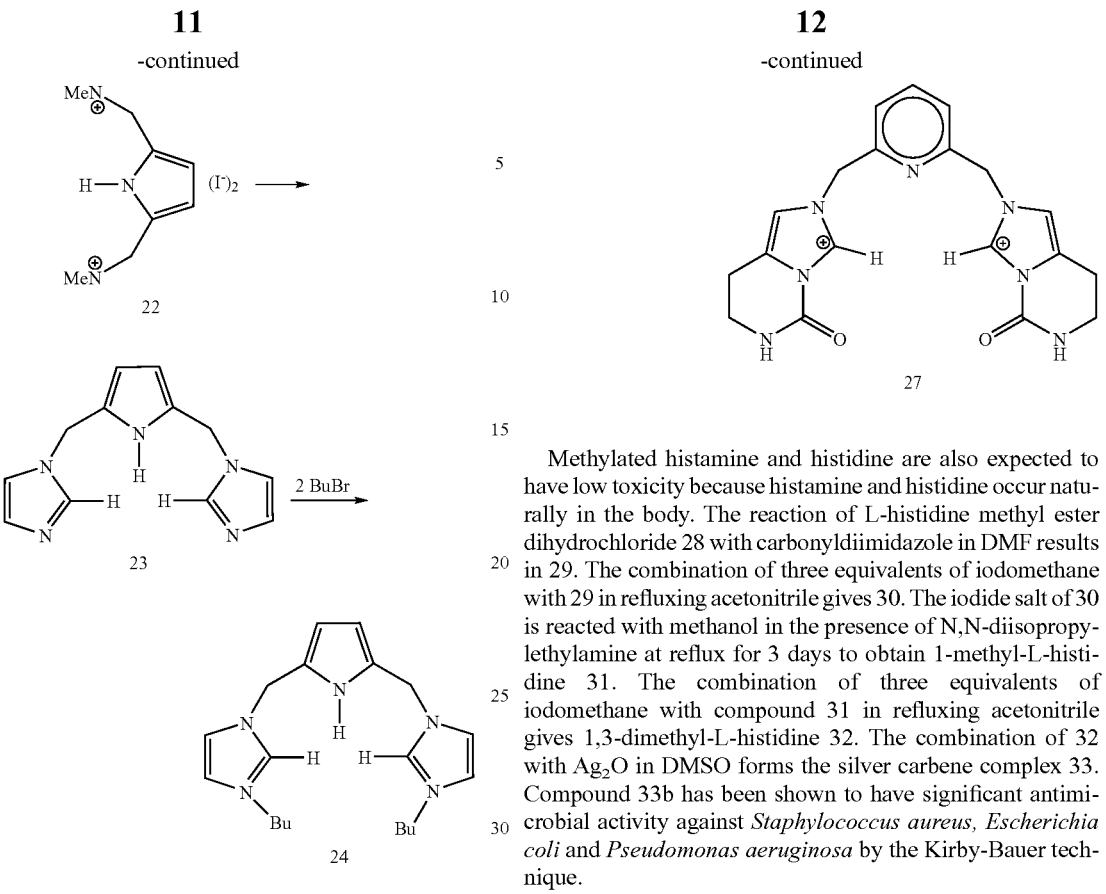

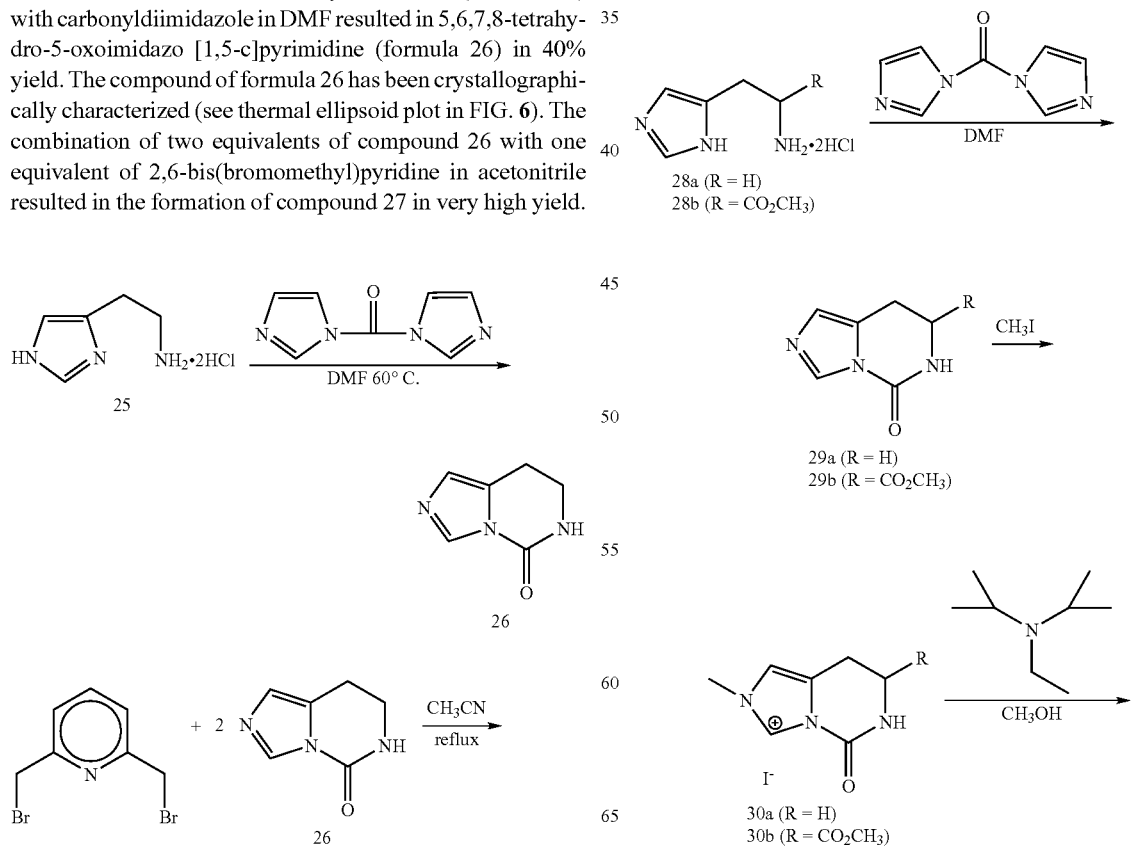

Methylated histidine and histidine are also expected to have low toxicity because histamine and histidine occur naturally in the body. The reaction of L-histidine methyl ester dihydrochloride 28 with carbonyldiimidazole in DMF results in 29. The combination of three equivalents of iodomethane with 29 in refluxing acetonitrile gives 30. The iodide salt of 30 is reacted with methanol in the presence of N,N-diisopropylethylamine at reflux for 3 days to obtain 1-methyl-L-histidine 31. The combination of three equivalents of iodomethane with compound 31 in refluxing acetonitrile gives 1,3-dimethyl-L-histidine 32. The combination of 32 with Ag$_2$O in DMSO forms the silver carbene complex 33. Compound 33b has been shown to have significant antimicrobial activity against *Staphylococcus aureus*, *Escherichia coli* and *Pseudomonas aeruginosa* by the Kirby-Bauer technique.

Figure 6:
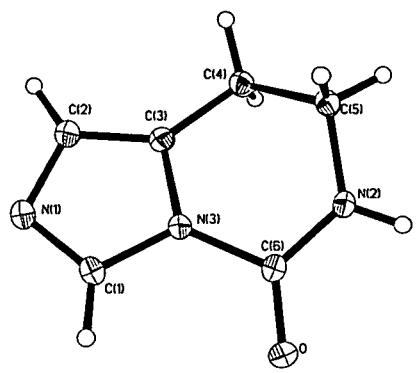
FIG. 6 is a thermal ellipsoid plot of 5,6,7,8-tetrahydro-5-oxoimidazo [1,5-c]pyrimidine shown as formula 26.
Figure 7:
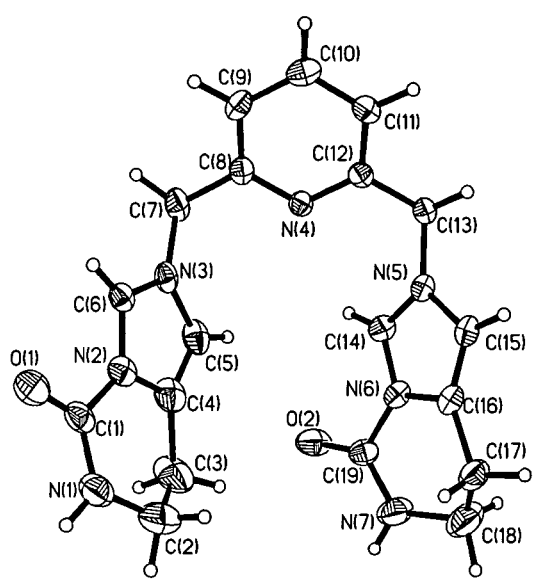
FIG. 7 is a thermal ellipsoid plot of the compound shown as formula 27.
Figure 8:
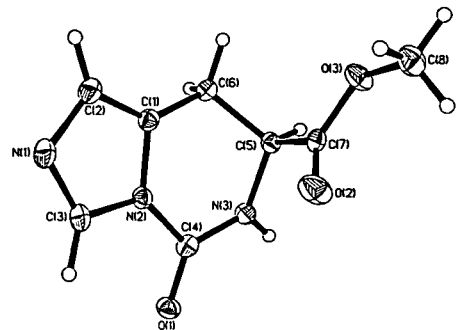
FIG. 8 is a thermal ellipsoid plot of the compound shown as formula 29b.
Figure 9:
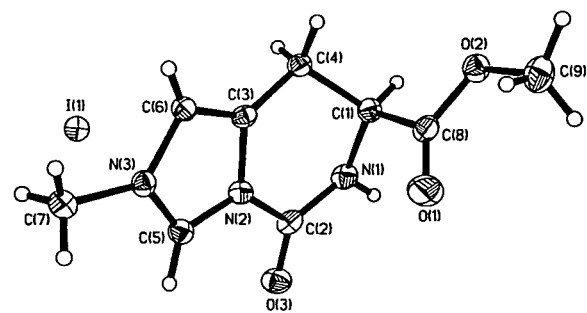
FIG. 9 is a thermal ellipsoid plot of the compound of the iodidie salt shown as formula 30b.

The reaction of histamine dihydrochloride (formula 25) with carbonyldiimidazole in DMF resulted in 5,6,7,8-tetrahydro-5-oxoimidazo [1,5-c]pyrimidine (formula 26) in 40% yield. The compound of formula 26 has been crystallographically characterized (see thermal ellipsoid plot in FIG. 6). The combination of two equivalents of compound 26 with one equivalent of 2,6-bis(bromomethyl)pyridine in acetonitrile resulted in the formation of compound 27 in very high yield.

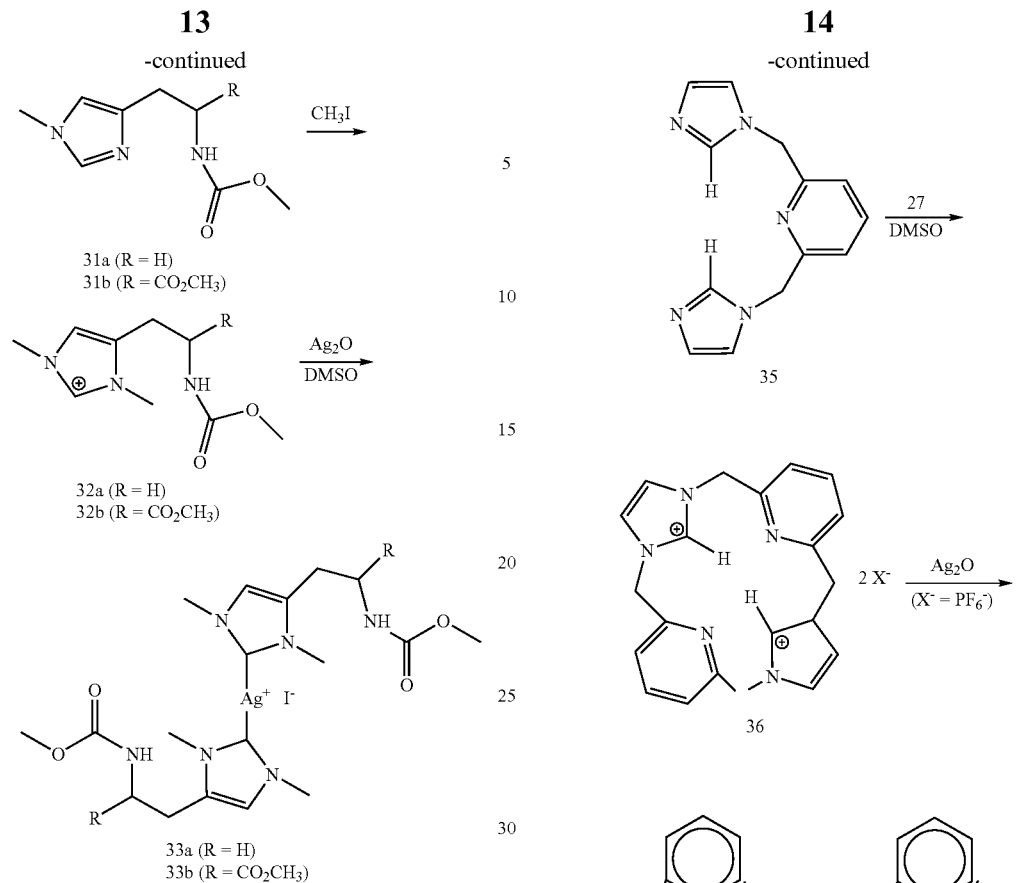

Figure 10:
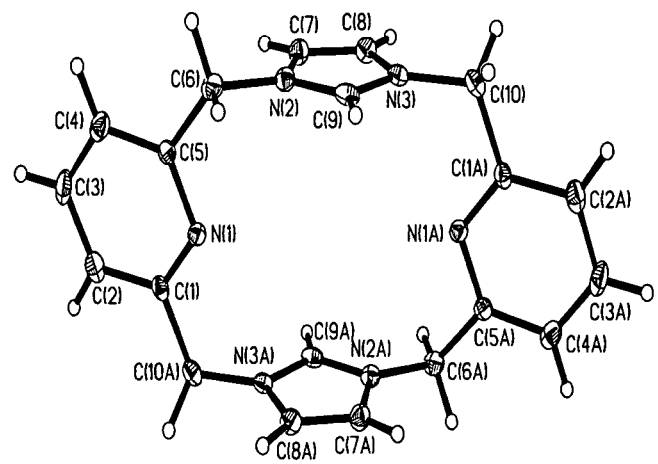
FIG. 10 is a thermal ellipsoid plot of [PF$_6^-$] salt of formula 36.
Figure 11:
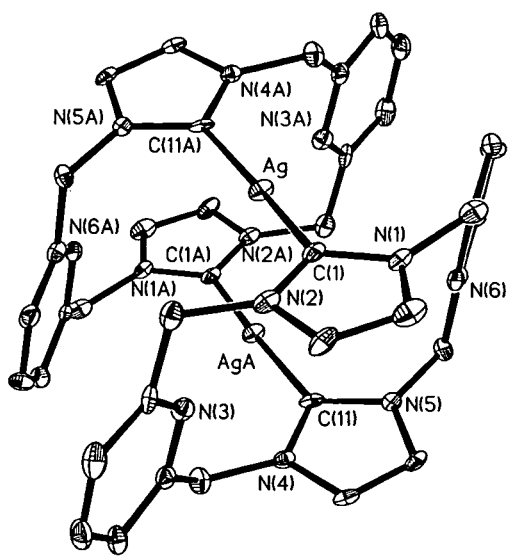
FIG. 11 is a thermal ellipsoid plot of the silver biscarbene dimmer shown as formula 37.
Figure 12:
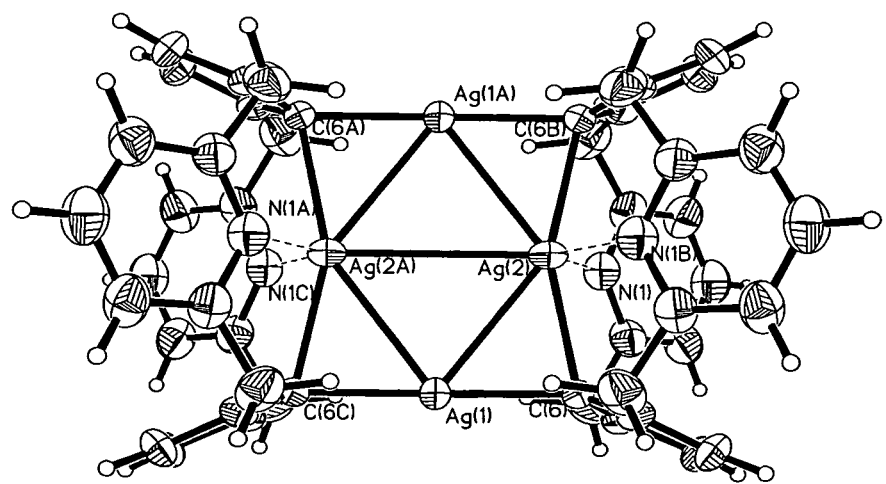
FIG. 12 is a thermal ellipsoid plot of the tetracationic portion of compound 38 [PF$_6^-$]$_4$.
Figure 13:
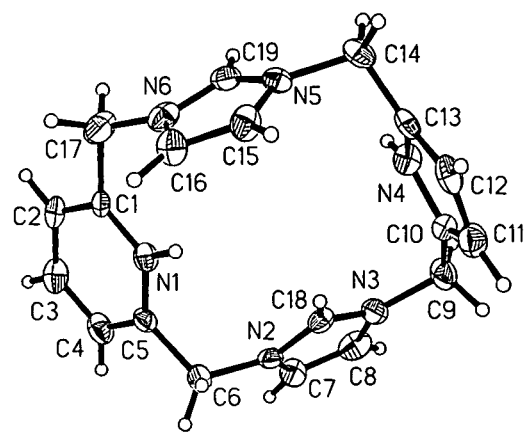
FIG. 13 is a thermal ellipsoid plot of the compound shown as formula 39b.

Macrocyclic N-heterocyclic carbenes may be synthesized according to the following method. The reaction of two equivalents of potassium imidazole with 2,6-bis(bromomethyl)pyridine (formula 34) resulted in the compound of formula 35 in 70% yield. The combination of compound 35 with compound 34 in DMSO gave the compound of formula 36 in 80% yield. The combination of the $PF_6^-$ salt of compound 36 with an equimolar amount of $Ag_2O$ gives a silver biscarbene dimer (formula 37) in nearly quantitative yield. Compounds 36 and 37 have been crystallographically characterized and are represented in FIG. 10 and FIG. 11 respectively. The bromide salt of compound 37 (X=Br), is soluble and stable in water. Under analogous reaction conditions, the combination of compound 36 with 4 equivalents of $Ag_2O$ gives a tetra-silver biscarbene dimer (not shown, but ref. to as formula 38 and FIG. 12). The combination of compound 36 (X$^-$=Br$^-$) with $Ag_2O$ in water directly gives the bromide salt of compound 37. Halide salts of compound 37 can be synthesized in water, and are water soluble. The bromide and chloride salts of compound 37 are effective antimicrobials.

Figure 14:
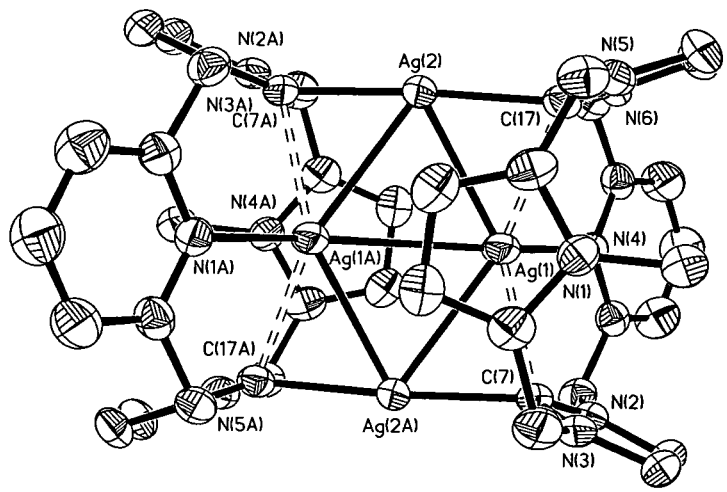
FIG. 14 is a thermal ellipsoid plot of the tetracationic portion of compound 40[PF$_6^-$]$_4$.

The 3+1 condensation of the pyrrole shown by formula 22 (R=H or Me), with the pyridine shown by formula 18 gives the compound of formula 39 (R=H or Me). Anion exchange of 39a with $NH_4^+PF_6^-$ gives compound 39b. The combination of 39b (X=$PF_6^-$, R=Me) with four equivalents of $Ag_2O$ gives a tetra-silver biscarbene dimer, compound 40 (X=$PF_6^-$, R=Me), the thermal ellipsoid plot of which is shown in FIG. 14.

-continued

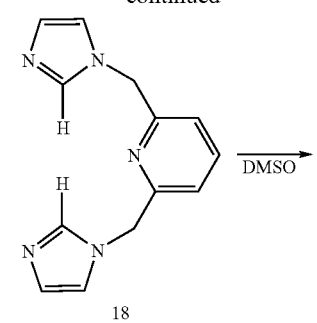

18

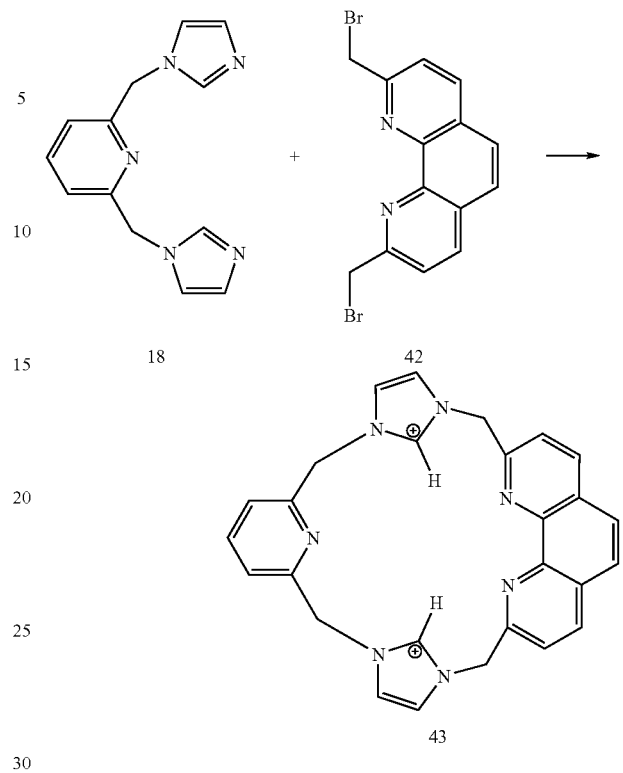

18    42

43

39a (X = I⁻, R = Me or H)
39b (X = PF₆⁻, R = Me or H)

40 (X = PF₆⁻, R = Me)
40 (X = PF₆⁻, R = Me)

Figure 15:
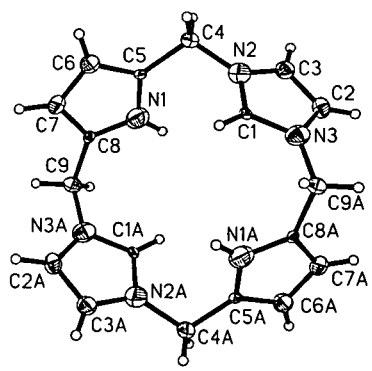
FIG. 15 is a thermal ellipsoid plot of the compound shown as formula 41.
Figure 16:
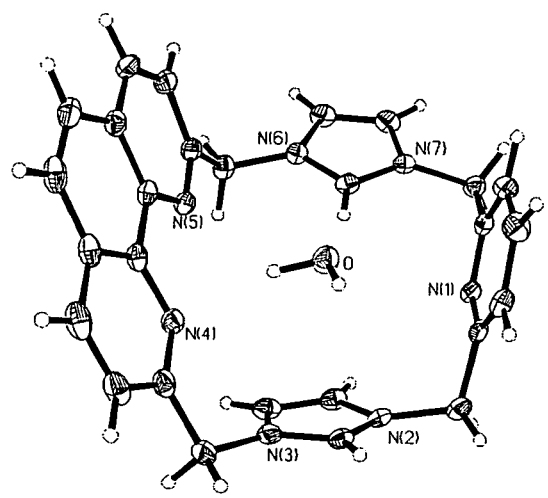
FIG. 16 is a thermal ellipsoid plot of the dibromide salt show as formula 43.
Figure 17:
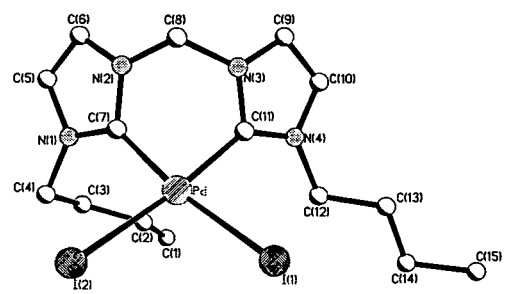
FIG. 17 is a thermal ellipsoid plot of the compound shown as formula 8c.
Figure 18:
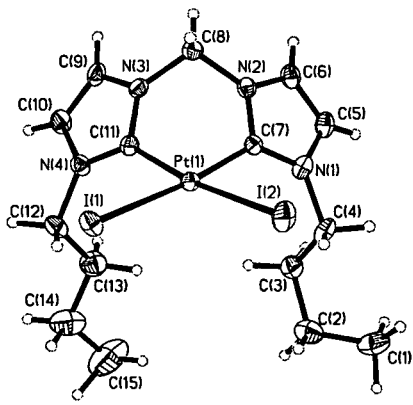
FIG. 18 is a thermal ellipsoid plot of the compound shown as formula 8d.
Figure 19:
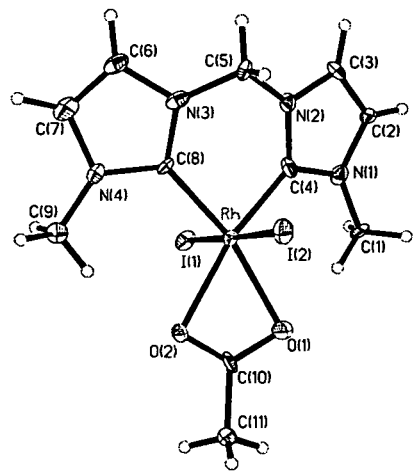
FIG. 19 is a thermal ellipsoid plot of the rhodium carbine shown as formula 8e.
Figure 20:
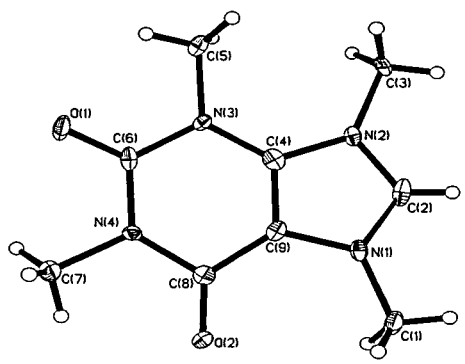
FIG. 20 is a thermal ellipsoid plot of the compound shown as formula 96b.
Figure 21:
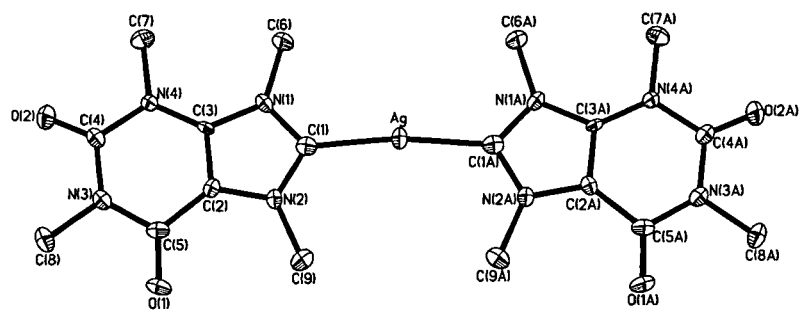
FIG. 21 is a thermal ellipsoid plot of the compound shown as formula 97b.
Figure 22:
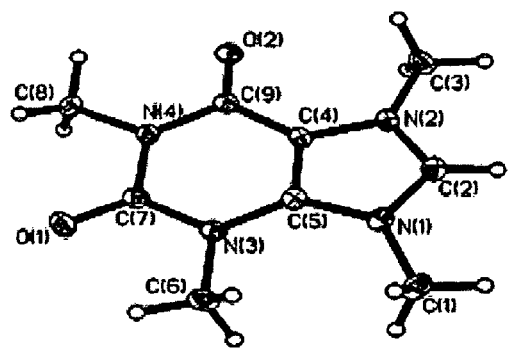
FIG. 22 is a thermal ellipsoid plot of the compound shown as formula 98.
Figure 23:
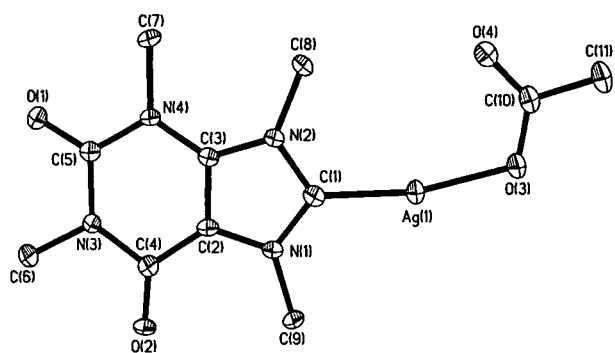
FIG. 23 is a thermal ellipsoid plot of the compound shown as formula 100.

Addition of one equivalent of compound 22 to compound 23 gives the bisimidazolium porphyrinoid 41 in high yield and on a large scale. Compound 41 has been crystallographically characterized and the thermal ellipsoid plot of the dication ring of 41 is shown as FIG. 15. The combination of compounds 39 (R=H) and 41 with 4 equivalents of Ag$_2$O affords tetra-silver biscarbene dimers analogous to compounds 38 and 40.

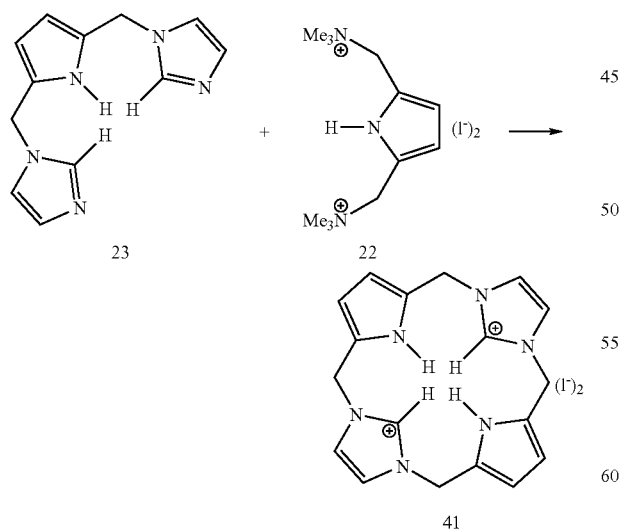

23    22

41

The combination of compound 18 with bis(bromomethyl) phenanthroline 42 affords the expanded macrocycle 43 as a dibromide salt.

Monodentate N-heterocyclic carbene silver complexes such as those represented by formula 48 may be synthesized by the interaction of the imidazolium precursors 44 with silver oxide. As mentioned above, the side chains, R, may be chosen so as to modify the water solubility, lipophilicity and other properties of the complexes. For example, R may be hydrogen or a $C_1$-$C_{12}$ organic group selected from the group consisting of alkyl, cycloalkyl, alkenyl, cycloalkenyl, alkynyl, aryl, arylalkyl, alkylaryl, heterocyclic, and alkoxy groups and substituted derivatives thereof. Silver complexes such as those represented by formulae 46 and 47, synthesized from histamine and histidine, respectively, may be synthesized and used as antimicrobial compounds. Because histamine and histidine are present in the body, their derivatives are expected to give the least skin irritation when used as a topical antimicrobial and to provide very limited problems as an internal antimicrobial with excellent toxicological properties.

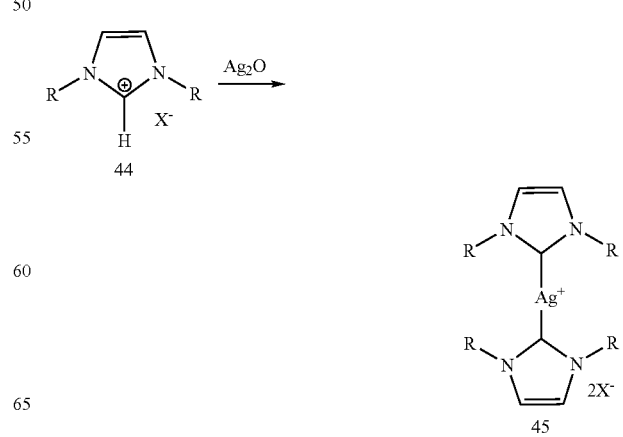

44

45

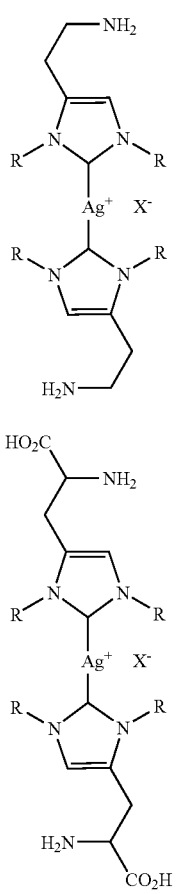

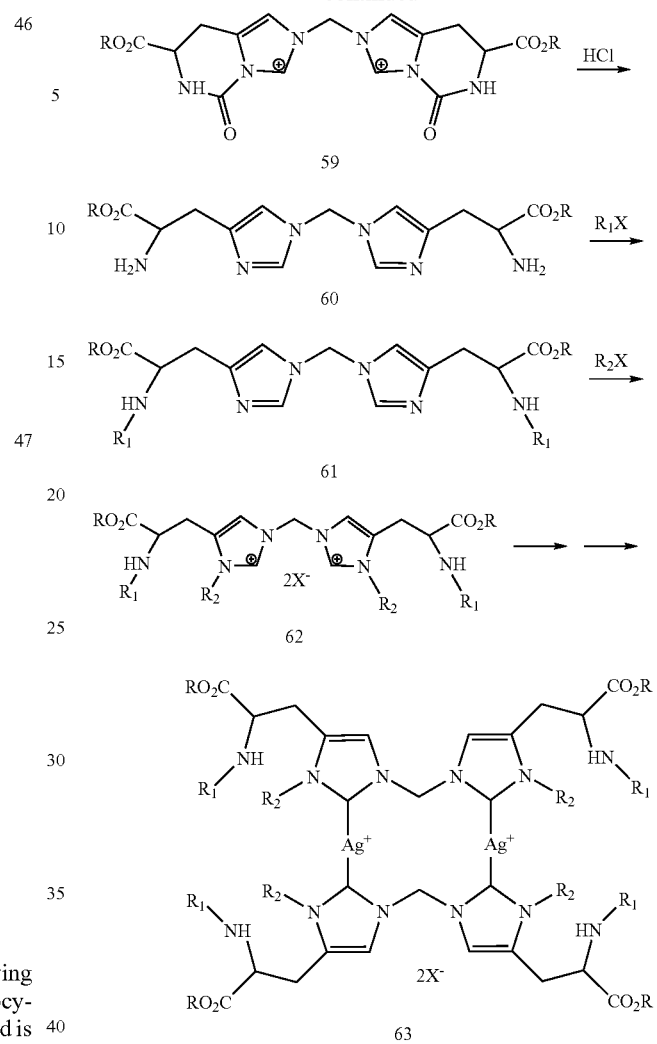

The synthesis of the pincer N-heterocyclic carbenes having methene or methylene groups bridging the two N-heterocyclic carbenes (see formula 3) and with substituents attached is provided below. The substituents may be chosen in order to give the overall complex sufficient solubility, lipophilicity or other properties. Pyridine rings and imidazoles serve as the fundamental building blocks in the procedures discussed below. Based on the synthesis of compounds 8a and 8b above, two equivalents of compound 58 will combine with methylene iodide to form compound 59. Opening of compound 59 with HCl will provide compound 60. One equivalent of an alkyl halide would readily add to the primary amines of compound 60, because primary amines are more reactive than imidazole nitrogens, to form compound 61. A second alkyl halide would add to the secondary imidazole nitrogens of compound 61 to form the bisimidazolium cation shown as compound 62. The bisimidazolium cation 62 may be combined with $Ag_2O$ to form silver complexes shown as formula 63 similar to compounds 9a and 9b above.

Compound 27 may be treated with HCl to give compound 64, which may then be contacted with a derivatized alkyl halide containing a solubilizing substituent to give compound 65. Compound 64 could also be derivatized with a carboxylic acid and dicyclohexylcarbodiimide (DCC) to form an amide bond. The combination of compound 65 at a higher temperature with a derivatized alkyl halide that similarly contains a solubilizing substituent will give the imidazolium biscation shown as formula 66, which may be further complexed with metals such as rhodium.

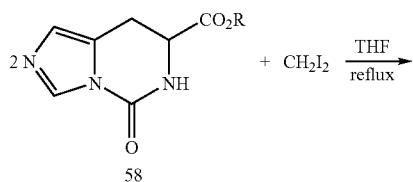

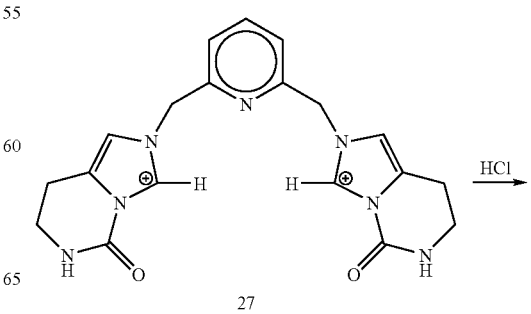

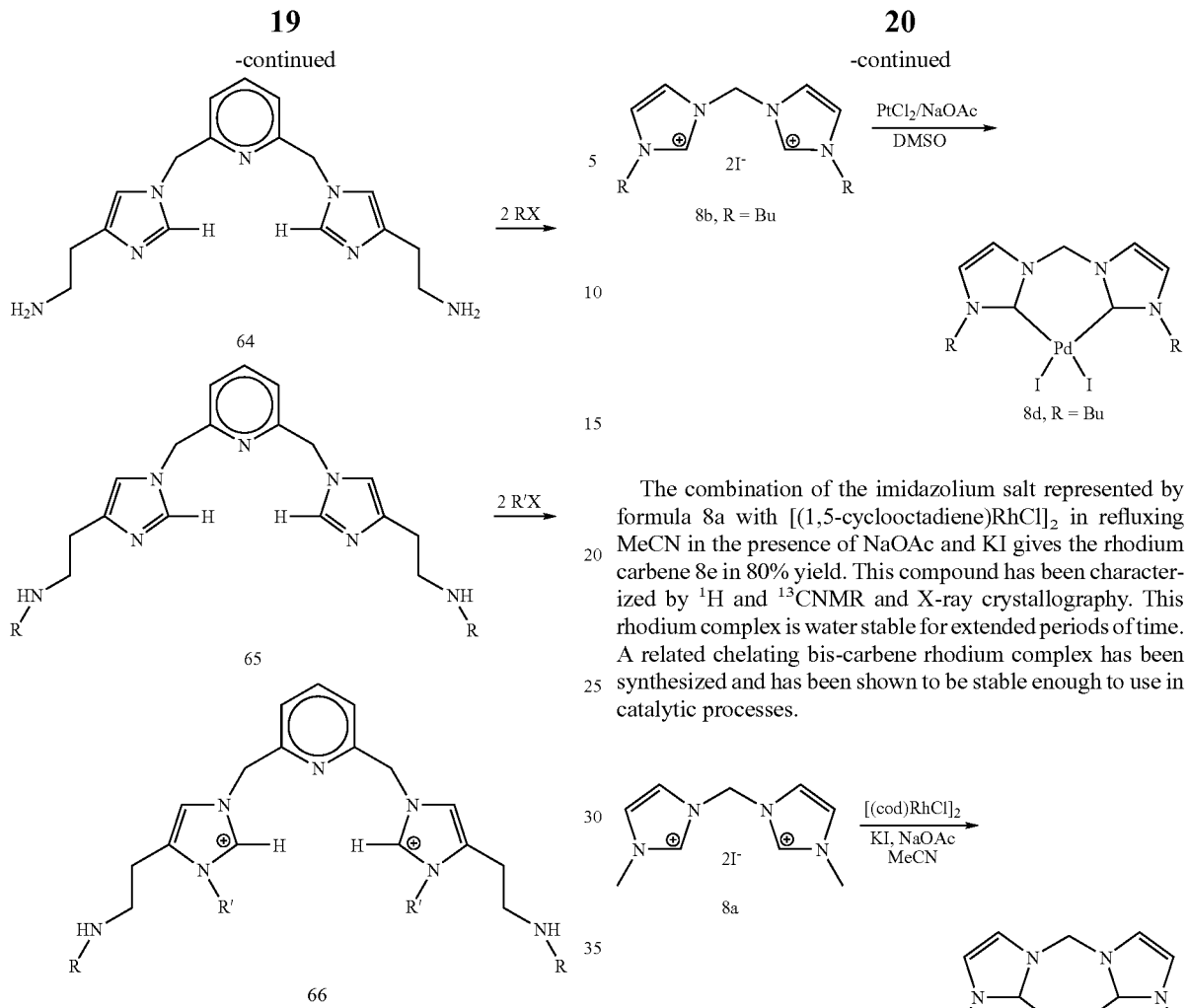

Silver-carbene complexes may also be used as carbene transfer reagents to create other carbene complexes. The formation of transition metal-carbene bonds, using carbene transfer reagents is favored in many situations because the reactions proceed under mild conditions and without the use of strong bases. For example, the combination of 8b with Pd(OAc)₂ in DMF followed by treatment with NaI in acetonitrile results in the formation of the compound represented by formula 8c. The thermal ellipsoid plot of this compound is shown below. Similarly, the combination of 8b with PtCl₂ and sodium acetate in DMSO gives the compound represented by formula 8d in 50% yield.

The combination of the imidazolium salt represented by formula 8a with [(1,5-cyclooctadiene)RhCl]₂ in refluxing MeCN in the presence of NaOAc and KI gives the rhodium carbene 8e in 80% yield. This compound has been characterized by ¹H and ¹³CNMR and X-ray crystallography. This rhodium complex is water stable for extended periods of time. A related chelating bis-carbene rhodium complex has been synthesized and has been shown to be stable enough to use in catalytic processes.

The silver complex of an N-heterocyclic carbene represented by formula 17 can function as a carbene transfer reagent. The reaction of complex 17 with (PhCN)₂PdCl₂ in CH₂Cl₂ yields the palladium carbene complex represented by formula 67 and two equivalents of AgCl in nearly quantitative yield.

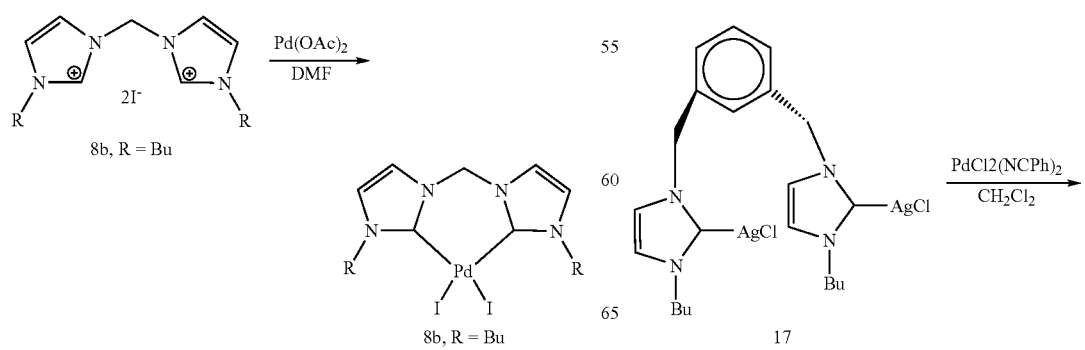

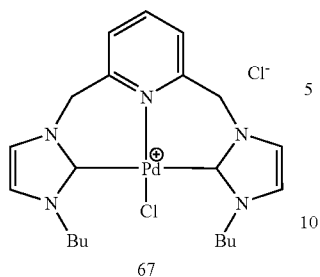

67

Similarly, the reaction of the complex represented by formula 20a with (PhCN)$_2$PdCl$_2$ in CH$_2$Cl$_2$ yields the palladium carbene complex represented by formula 68.

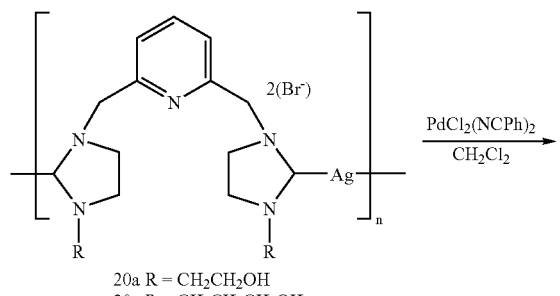

20a R = CH$_2$CH$_2$OH
20a R = CH$_2$CH$_2$CH$_2$OH

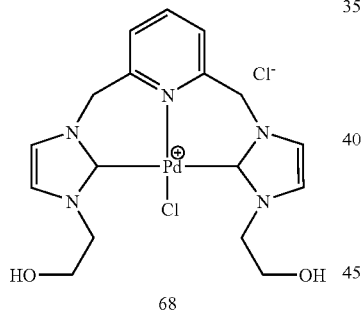

68

A similar synthesis route may be used to synthesize the compound represented by formula 69 from the compound represented by formula 19a.

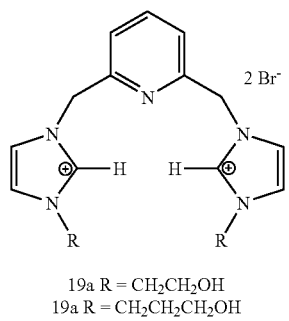

19a R = CH$_2$CH$_2$OH
19a R = CH$_2$CH$_2$CH$_2$OH

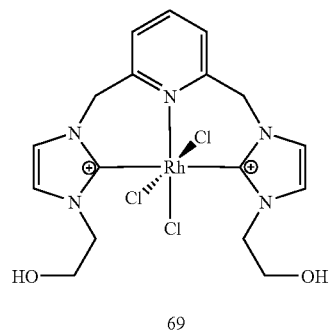

69

For the synthesis of pyrrole bridged pincer N-heterocyclic carbenes, a 2,5-bisdimethylpyrrole with leaving groups on the methyl groups is particularly useful in the synthesis method of the present invention. The Mannich reaction of dimethylammonium chloride in aqueous formaldehyde and pyrrole gives 2,5-bisdimethylaminomethylpyrrole, represented by formula 70. Addition of iodomethane to pyrrole 70 in THF gives 2,5-bis(trimethylaminomethyl)pyrrole diiodide (formula 71).

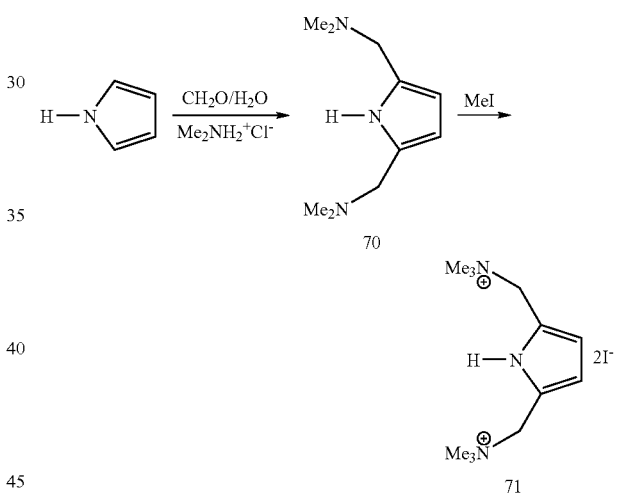

A molecule containing a 2-nitroimidazole group is believed to be targeted to hypoxic cells. These compounds are reduced at the nitroimidazole group and trapped within cells with a low oxygen environment. Attachment of a 2-nitroimidazole group to pincer N-heterocyclic carbenes to form the compound represented by formula 73 may be accomplished as follows. The condensation of the compound represented by formula 72 with bisimidazol in a 2:1 ratio is expected to give the compound represented by formula 73. Other derivatives of 2-nitroimidazole having various linker segments may similarly be synthesized. The variety of linker groups, including polyethylene oxide (PEO), will allow for flexibility in positioning the chelator relative to the targeting group as well as for variation of the octanol/water partition coefficient of the compound, which is relevant to the clearance through the kidneys. The formation of rhodium complexes similar to 73 is also envisioned. Similar procedures may be used to synthesize derivatives of 75 and 76 containing nitroimidazole and solubilizing substituents.

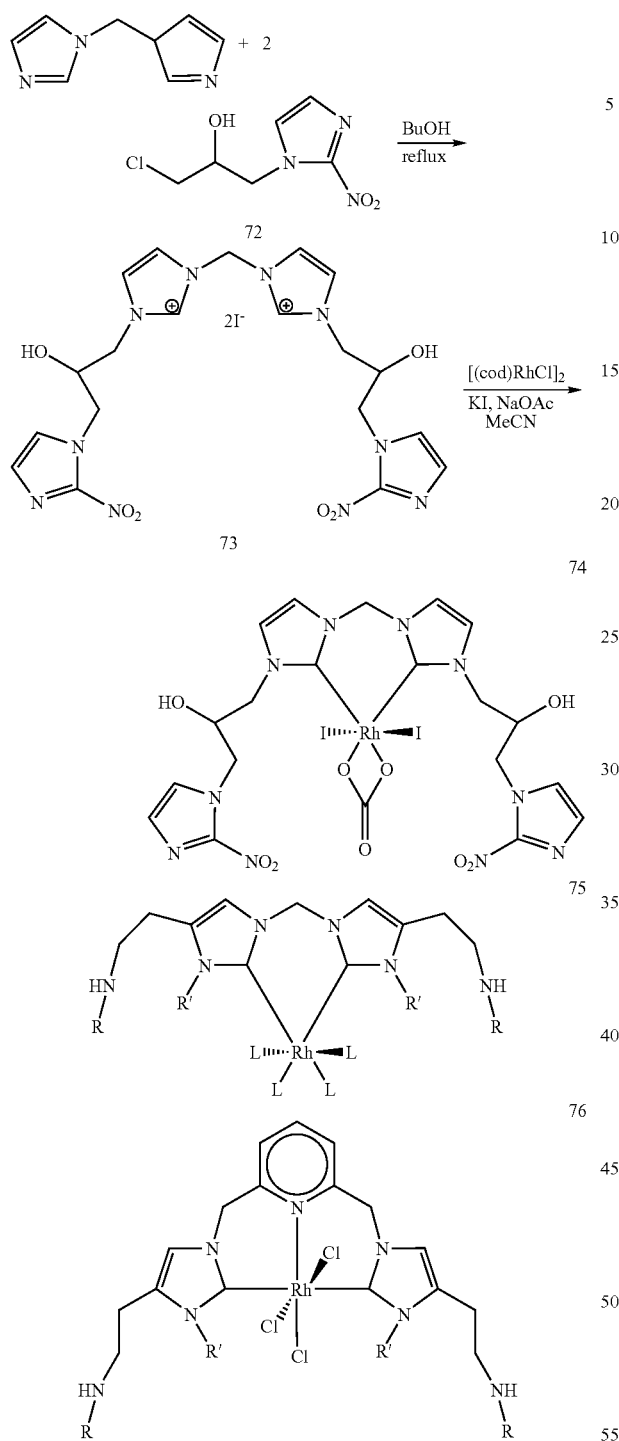

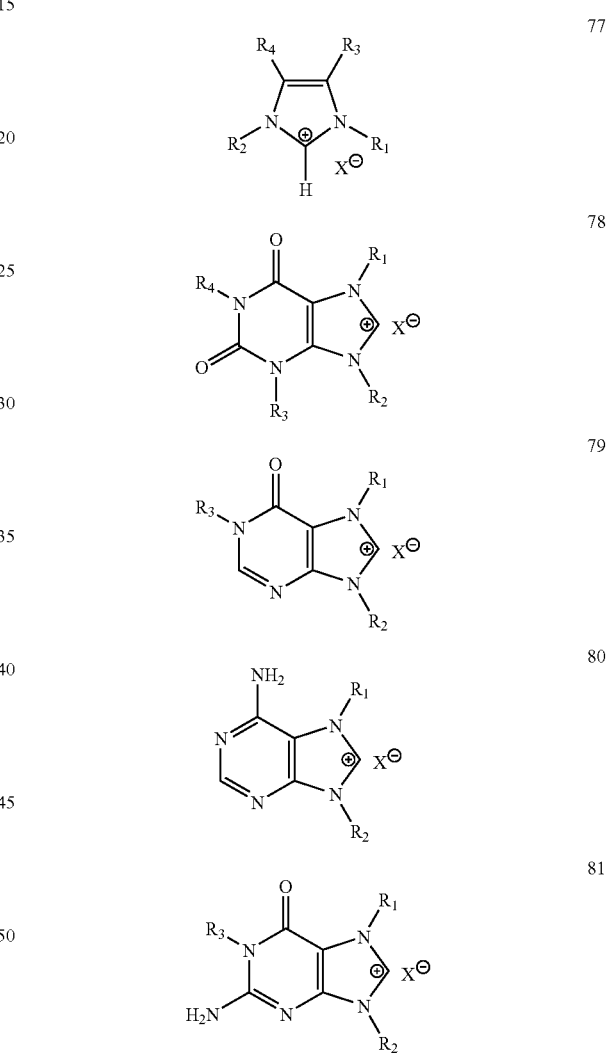

As mentioned above, the present invention includes metal N-heterocyclic carbene complexes that can be made from several N-heterocyclic carbene precursors, the imidazolium salts. The imidazolium salts obtained from biological analogs, such as the purine bases which includes xanthine, hypoxanthine, adenine, guanine and there derivatives can readily be reacted with silver(f) oxide in suitable solvent to obtain the silver-N-heterocyclic carbene complexes. The imidazolium cations can easily be classified as mono-imidazolium cation such as those represented by formulae 77-81, bis-imidazolium cations such as those represented Isotopes of the metals indicated herein as components of an N-heterocyclic carbene complex may be used to form radiopharmaceuticals. For example, $^{105}$Rh may be used in place of Rh. $^{105}$Rh has a convenient half-life of 1.5 days and also emits relatively low levels of γ-radiation. This isotope of rhodium decomposes by beta emission to $^{105}$Pd a stable naturally occurring isotope of palladium. Other employable isotopes can be selected from transition metals, elements from the lanthanide series, and elements from the actinide series. Preferred isotopes are Ag, Rh, Ga, and Tc.

Preferable mono-imidazolium cations include those represented by formulae 48-52:

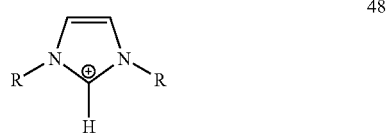

49

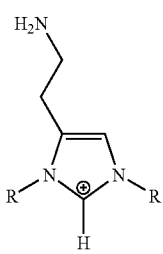

50

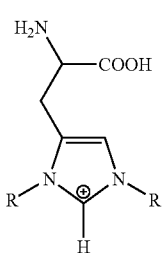

51

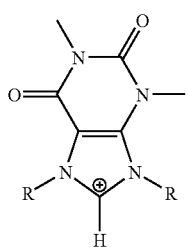

52

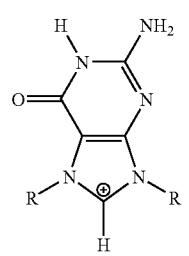

which can be used for the formation of preferred monodentate N-heterocyclic carbene silver complexes, such as those having formulae 53-57, respectively. The carbene silver complexes shown in formulae 53-57 can be synthesized by the interaction of the imidazolium precursors 48-52, respectively, with a silver oxide:

53

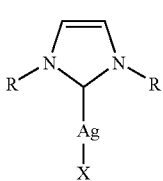

54

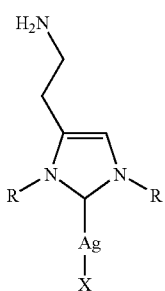

55

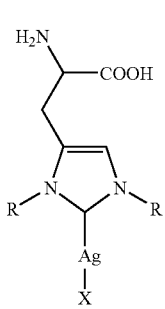

56

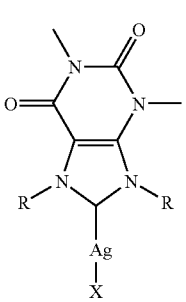

57

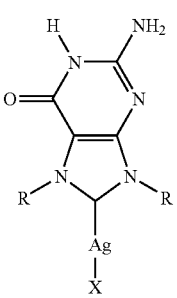

Similarly, multi-imidazolium cations according to the present invention include those represented by formulae 82-90:

82

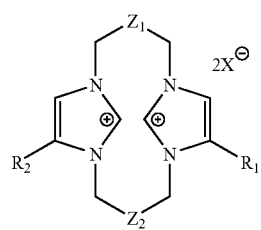

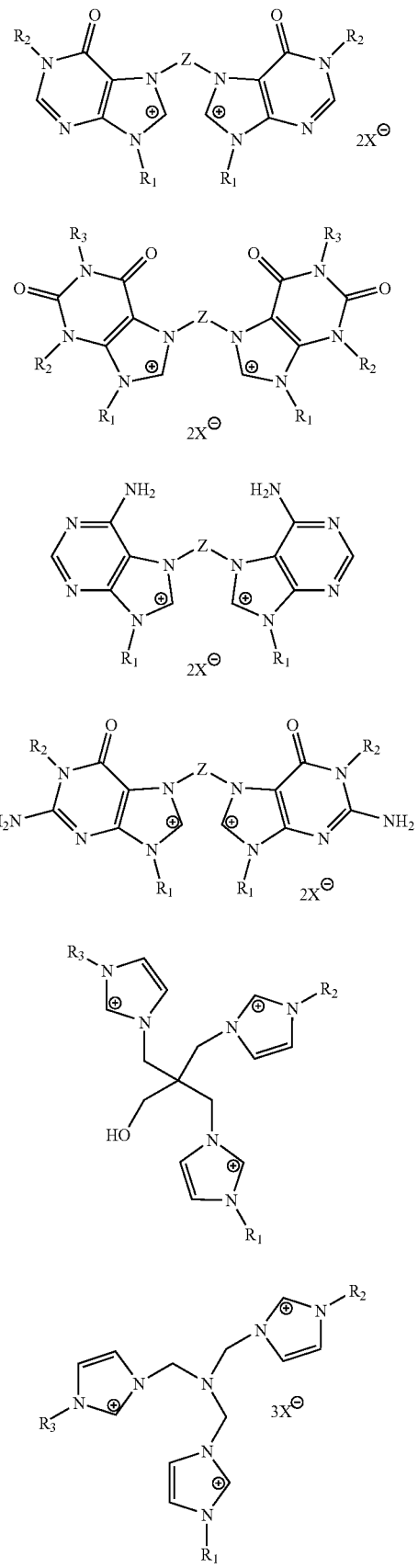

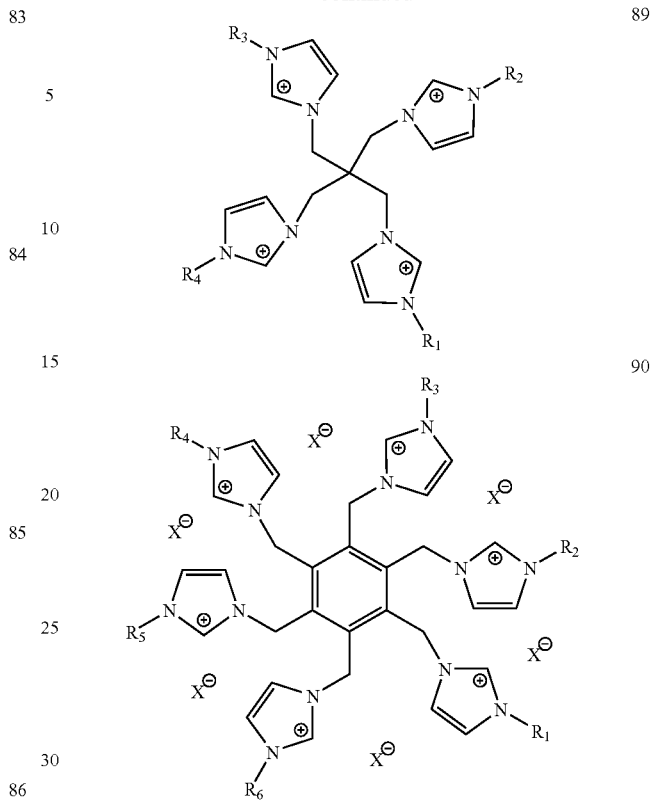

The bis-imidazolium cations bridged may be represented by Z. Wherein Z can be a methylene, heterocyclic group, dimethyl heterocyclic group, dimethyl cycloalkane group, dimethyl substituted heterocyclic group, aryl group, dimethyl substituted aryl group. The bis-imidazolium cations can be bridge by $Z_1$ and $Z_2$ to form a ring (cyclophane), wherein $Z_1$ and $Z_2$ can each be separate or in combination, and may be selected from the group consisting of heterocyclic, $C_1$-$C_{12}$ substituted heterocyclic, aryl, $C_1$-$C_{12}$ substituted aryl, $C_3$-$C_{12}$ substituted ketone, and $C_1$-$C_{12}$ alkylene groups. Each R group; $R_1$, $R_2$, $R_3$ and $R_4$ functionality, and the counter anion X of the imidazolium salt may be modified to improve the lipophilicity of compound. The $X^-$ counter anion may be from the group consisting of halides, carbonate, acetate, phosphate, hexafluorophosphate, tetrafluoroborate, nitrate, methylsulfate, hydroxide and sulfate. Each R group ($R_1$, $R_2$, $R_3$ and $R_4$), separately or in combination, may be selected from the group consisting of hydrogen, $C_1$-$C_{12}$ alkyl, $C_1$-$C_{12}$ substituted alkyl, $C_1$-$C_{12}$ alkoxy, $C_1$-$C_{12}$ cyclo alkyl, $C_1$-$C_{12}$ substituted $C_1$-$C_{12}$ cyclo alkyl, $C_1$-$C_{12}$ alkenyl, $C_1$-$C_{12}$ cycloalkeny, $C_1$-$C_{12}$ substituted cycloalkenyl, $C_1$-$C_{12}$ alkynyl, $C_1$-$C_{12}$ aryl, $C_1$-$C_{12}$ substituted aryl, $C_1$-$C_{12}$ arylalkyl, $C_1$-$C_{12}$ alkylamine, $C_1$-$C_{12}$ substituted alkylamine, $C_1$-$C_{12}$ alkylpentose phosphate, $C_1$-$C_{12}$ phenols, and $C_1$-$C_{12}$ esters. The selection of $R_1$, $R_2$, $R_3$, and $R_4$ functionality is desirable in some of its pharmaceutical applications.

Purines are also being examined as carbene precursors for carrying silver. Of particular interest is guanine, one of the nucleobases in DNA. Guanine 91 has a ring system similar to that of caffeine 95. Since guanine is non-toxic it seems reasonable that 7,9-dimethylguanine would have low toxicity. This makes the dimethyl guanine ligand very attractive for cystic fibrosis research because we are looking for non-toxic as well as small ligands to serve as carriers for silver cations.

Dimethylation of guanine 91 with dimethylsulfate followed by treatment with ammonium hydroxide gives the water insoluble 7,9-dimethylguanine zwitterion 92. Addition of HBr to the zwitterion 92 gives the bromide salt 93. The bromide salt is soluble in water and is precipitated out using THF. The silver complex is formed by suspending the bromide salt in DMSO, adding Ag$_2$O to the solution and heating at 60-80° for about 6 hours.

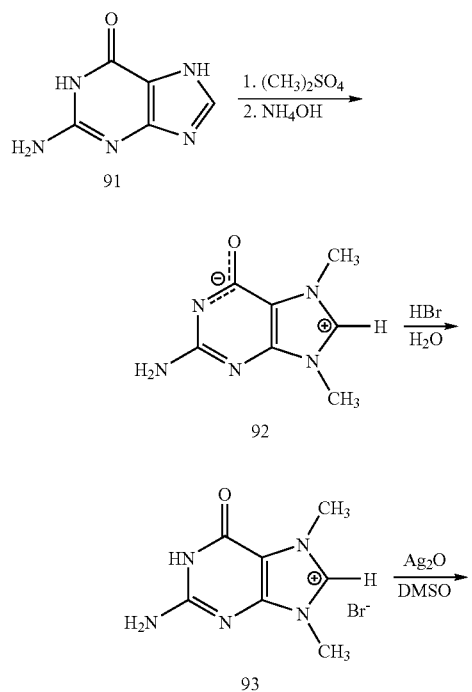

Xanthines have been used for a number of years as bronchodilators for the treatment of airway obstructions in cystic fibrosis patients. Because xanthines contain imidazole rings we assumed it should be possible to alkylate them to form imidazolium cations and eventually silver carbene complexes. Because of their use as bronchodilators we also assumed that their methylated derivatives would be relatively nontoxic. Probably the most well know of the xanthines is caffeine 95. We have investigated the alkylation of caffeine to form methylated caffeine and the formation of silver carbene complexes using caffeine as the carbene precursor. Methylated caffeine has proven to be even less toxic than caffeine.

The methyl sulfate salt of methylated caffeine, 1,3,7,9-tetramethylxanthanium, 96a is given by the reaction of caffeine 95 with dimethyl sulfate in nitrobenzene. Anion exchange using NH$_4$PF$_6$ in water results in 96b.

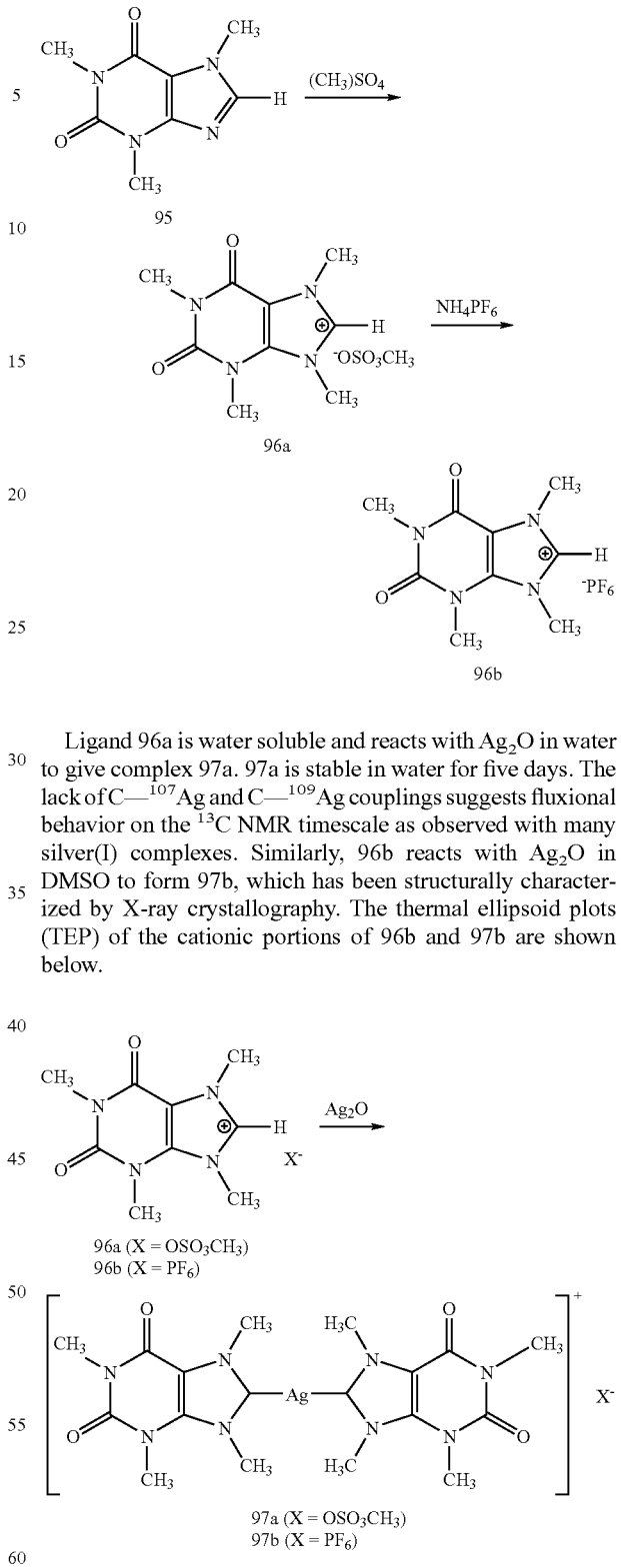

Ligand 96a is water soluble and reacts with Ag$_2$O in water to give complex 97a. 97a is stable in water for five days. The lack of C—$^{107}$Ag and C—$^{109}$Ag couplings suggests fluxional behavior on the $^{13}$C NMR timescale as observed with many silver(I) complexes. Similarly, 96b reacts with Ag$_2$O in DMSO to form 97b, which has been structurally characterized by X-ray crystallography. The thermal ellipsoid plots (TEP) of the cationic portions of 96b and 97b are shown below.

Caffeine, 1,3,7-trimethylxanthine, is one of the xanthine derivatives that are generally used in medicines as diuretics, central nervous system stimulants and inhibitors of cyclic adenosine monophosphate (c-AMP) phosphodiesterase. 1,3,7,9-tetramethylxanthinium iodide (methylated caffeine), an imidazolium salt, was synthesized using modified literature procedures and characterized by $^1$H, $^{13}$C NMR, mass spectrometry and X-ray crystallography.

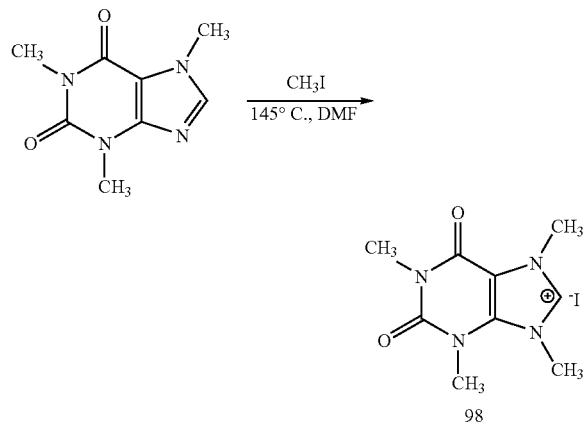

The reaction of two equivalent of 1,3,7,9-tetramethylxanthinium iodide with three equivalent of silver(I) oxide in methanol at room temperature gives compound 99.

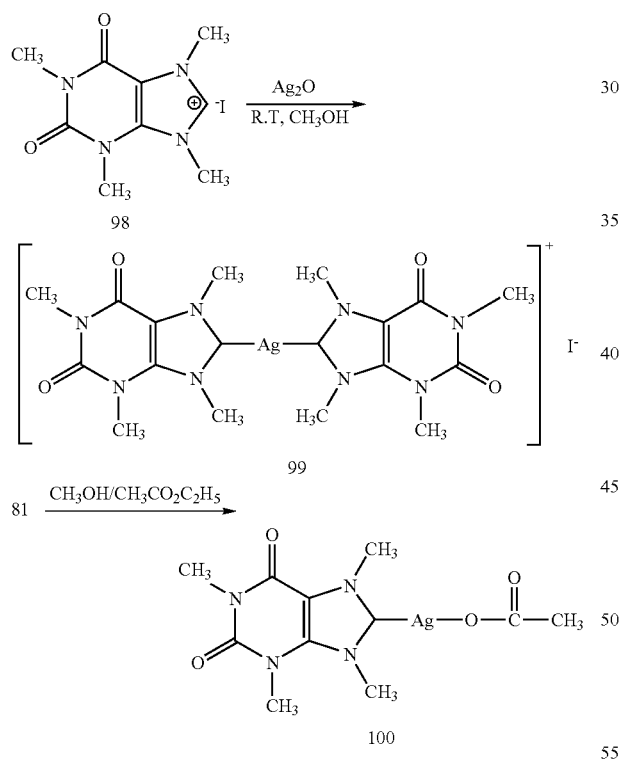

The crystallization of 99 in a mixture of methanol and ethyl acetate gives compound 100, a colorless crystal, soluble in water and air stable. Compounds 99 and 100 were characterized by $^1$H, $^{13}$C NMR, and mass spectrometry. X-ray crystallography was used to confirm the molecular structure of 100 with the thermal ellipsoid plot show above. The antimicrobial properties of 100 have been evaluated using both the filter disk test and the standard MIC technique. Compound 100 was found to have effective antimicrobial activity on S. aureus, P. aeruginosa, and E. coli. The dose-response effect on compound 98 was assessed to determine the toxicity of the compound on rats. The toxicity study, is a standard protocol used to determine the lethal dose required to kill half (LD 50) of the animals (rats). The LD 50 assessment on compound 98 was 2.37 g per Kg of rat. The protocol used in this study was approved by the Institutional Animal Care and Use Committee (IACUC), University of Akron.

The delivery methods for administering an effective amount of transition metal complexes of N-heterocyclic carbenes for in-vitro and in-vivo medicinal application consist of aerosol, biodegradable polymers, polymeric micelles, hydrogel types materials, dendrimers, and modified C-60 fullerenes.

The reaction shown resulting in the silver carbine complex 202 is similar in nature to the silver carbine complex previously shown in 100. 202 is an additional silver complex of xanthine

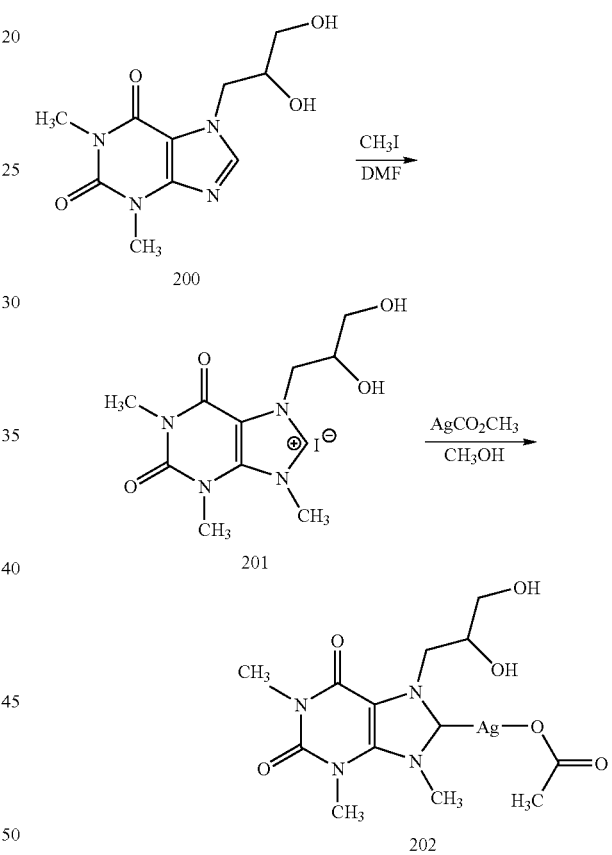

derivative, namely 7-(2,3-dihydroxypropyl)theophylline silver(I) complex. 202 is a derivative of theophylline complexed with Ag (I) that has a $K_{sp}$ of 82 mg/mL (attributable to the hydroxyl group), and is stable in solid form for months. Synthesis of 202 is straightforward and adaptable to large scale production.

The imidazolium salt 1,3,9-trimethyl-7-(2,3-dihyroxypropyl)xanthinium iodide 201 is obtained by reacting 7-(2,3-dihydroxypropyl)theophylline 200 with methyl iodide in dimethylformamide. The imidazolium salt 201 reacts with silver acetate in methanol to give the N-heterocyclic carbene silver(I) acetate complex, 202, as a white solid in 34% yield (structure confirmed by X-ray crystallography). 202 is water soluble ($K_{sp}$=82 mg/mL) and is stable for greater than 7 days in water by NMR. As 202 decomposes to release Ag$^+$ it regenerates the cationic portion of 201. The imidazolium cation portion of compound 201 has an $LD_{50}$ in rats of >2.0 g/kg in preliminary studies.

202 has a shelf life of several months at room temperature. Each portion of 202 can be readily reconstituted in sterile water to form a clear, colorless solution with a concentration of 10 mg/mL.

In addition to the imidazole ring portion that is converted into a carbine for binding metals, the feature common to 100, 202 and the generic form 56 is the presence of a bis amide ring on the "backside" of the imidazole-carbene portion. This bis amide ring is electron withdrawing. Silver acetate carbine complexes that do not contain electron-withdrawing groups in the ring are not as stable to water as are 100 and 202.

The minimum inhibitory concentrations (MIC) of the silver carbine 202 for a panel of *E. coli* from a variety of sources was determined (*Escherichia coli* being the leading cause of urinary tract infections). Strains influenced included the sequenced cystitis strain UTI89 and pyelonephritis strain CFT073; the sequenced laboratory *E. coli* strain MG1655; and seven strains from patients with acute or recurrent UTIs or asymptomatic bacteriuria. Overnight Luria broth (LB) cultures of these strains were subcultured 1:100, grown 2-3 hours to $OD_{600\ nm}=0.4$, and diluted 1000-fold in fresh LB. One hundred μL of each suspension was added to 100 μL of a range of dilutions of 202 in wells of a 96-well plate. After 16 h static incubation at 37° C., MICs were assessed visually and by quantitative absorbance measurement in a microplate reader at 600 nm. The MIC of 202 against this panel of strains was generally 2-4 μg/mL, similar to that observed against *P. aeruginosa* and *Burkholderia* species.

A prerequisite for a topical biocide is that it confers acceptable toxicity to the tissue(s) of interest. In vitro toxicity of 202 has been studied using the bladder carcinoma-derived T24 epithelial cell line (ATCC HTB-4). T24 cells were grown in RPMI 1640 medium available from Life Technologies (Carlsbad, Calif.) supplemented with 10% fetal bovine serum available from Sigma (St. Louis, Mo.), seeded into 24-well plates, and grown to confluence over 48 h. Cells were washed with sterile phosphate buffered saline (PBS) and fresh warmed medium was added, either alone or containing 202 (added to the medium at the start of the experiment to minimize premature liberation of $Ag^+$ from 202) at concentrations between 5 and 50 μg/mL. After incubation for 1-2 h, cells were released by treatment with 0.05% trypsin—0.02% EDTA, suspended in sorting buffer, stained with propidium iodide, and subjected to flow cytometry on a FACS Calibur instrument available from Becton Dickinson (Piscataway, N.J.). Our initial experiments demonstrate that loss of viability is ~5% after 1 h of treatment with 202 at 5 μg/mL and ~11% after 2 h of such treatment.

Additional work has explored the addition of electron-withdrawing groups on the "backside" of the carbene moiety, which provides augmented stability to sodium, chloride, and other ions. Deprotonation of 205 with potassium hydroxide followed by double methylation with methyl iodide gives the N-heterocyclic carbene 206. The bis(NHC) silver(I) complex 208 was formed from the reaction of the nitrate salt 207 with an excess of silver(I) oxide in acetonitrile.

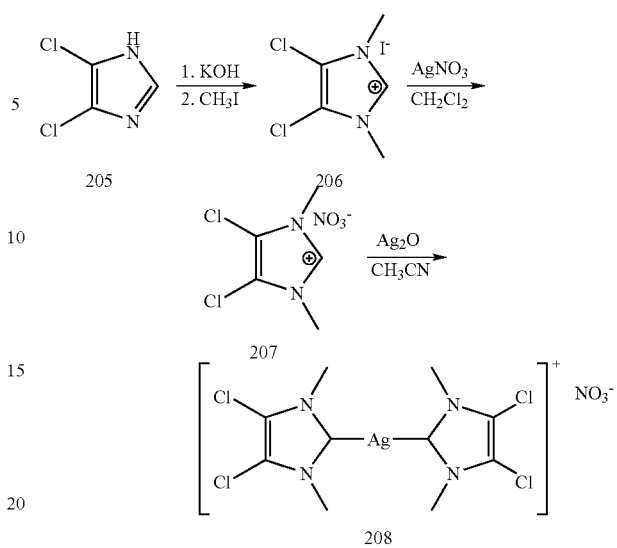

The bis(NHC) silver(I) complex, 210, with an iodide anion was added to 0.9% sodium chloride solution (equivalent to physiological serum $Na^+$ concentration). The solution was decanted and the resulting precipitate was dissolved in acetone. Slow evaporation of acetone gave white crystals of 211 that show bridging chlorides and a silver NHC bond still intact. The stability of 211 to physiological concentrations of sodium chloride is unprecedented. In addition to stabilizing silver NHCs to water, the presence of electron-withdrawing groups on the imidazole ring can greatly enhance their stability to physiological sodium chloride. This type chemistry is particularly suited for use in the urinary tract, where urinary osmolality in humans may vary from 300-1200 mOsm/L.

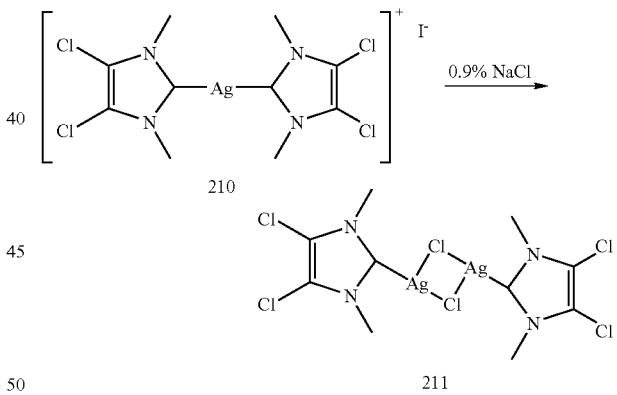

As stated above, the major advantage of SCs over earlier silver compounds is their stability and solubility in water. The addition of electron-withdrawing groups on the "backside" of the carbene component provides augmented stability to ionic strength, such as might be found in the urinary tract.

The 4,5-dihaloimidazoles, 215, were also explored for their ability to form stable silver NHC complexes. The imidazolium salt 216 is synthesized using the appropriate methylating agents. Imidazole starting materials with other electron-withdrawing groups such as nitro and cyano groups, 217, are examined. The dinitro and dicyano analogs of 217 are commercially available and synthesis of the cyano-nitro analog is known. The imidazolium salts of these compounds, 218, are synthesized according to the general procedure outlined as before. Compounds 216 and 218 are then be combined with silver acetate and silver oxide to form new silver carbene using procedures discussed above.

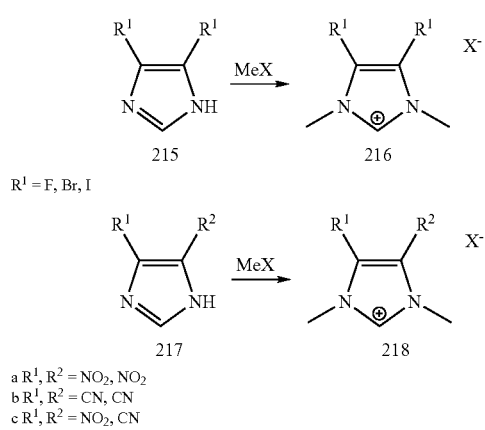

$R^1$ = F, Br, I a $R^1, R^2$ = $NO_2, NO_2$
b $R^1, R^2$ = CN, CN
c $R^1, R^2$ = $NO_2$, CN

The delivery methods for administering an effective amount of silver complexes of N-heterocyclic carbenes for in-vitro and in-vivo medicinal application consist of (or include) aerosol, biodegradable polymers, polymeric micelles, hydrogel types materials, dendrimers, and modified C-60 fullerenes. The silver carbine complexes are used in an amount from 0.01 μg to 600 mg. The preferred delivery method for treating urinary tract infections using silver carbine complexes involves dissolving the silver carbene complex into a fluid such as, but not limited to, water or saline. Water and saline are preferred due to their compatibility with the human body, but other fluids that are compatible can be used as well. The silver carbine complex solution is instilled into the urinary bladder via an instrument such as, but not limited to, a urinary catheter. A normal sized urinary bladder in an adult human is 500 to 600 mL. The preferred amount of fluid used in treatment of urinary tract infections is 1 to 600 mL, another preferred range is 25 to 450 mL, and another preferred range is 80 to 300 mL. The preferred concentration of the silver carbine complex in fluid is in the range of 0.01 to 1000 μg/mL, another preferred range is 0.5 to 100 μg/mL and another preferred range is 1 to 25 μg/mL.

Regarding urinary tract infections the terms treating and/or treatment include resolving an existing urinary tract infection.

In order to demonstrate the practice of the present invention, two N-heterocyclic carbenes 101 and 102 were synthesized and tested for antimicrobial properties as described below. The compounds can be shown with reference to formula 4

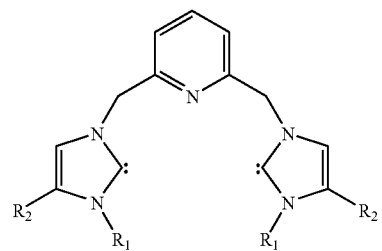

where $R_1$ is a hydroxyethyl or hydroxypropyl group and $R_2$ is a hydrogen atom. These carbenes 101 and 102 were synthesized by reacting 2,6-bis-(imidazolmethyl)pyridine with either 2-iodoethanol or 3-bromopropanol to provide compounds of formulas 101 and 102.

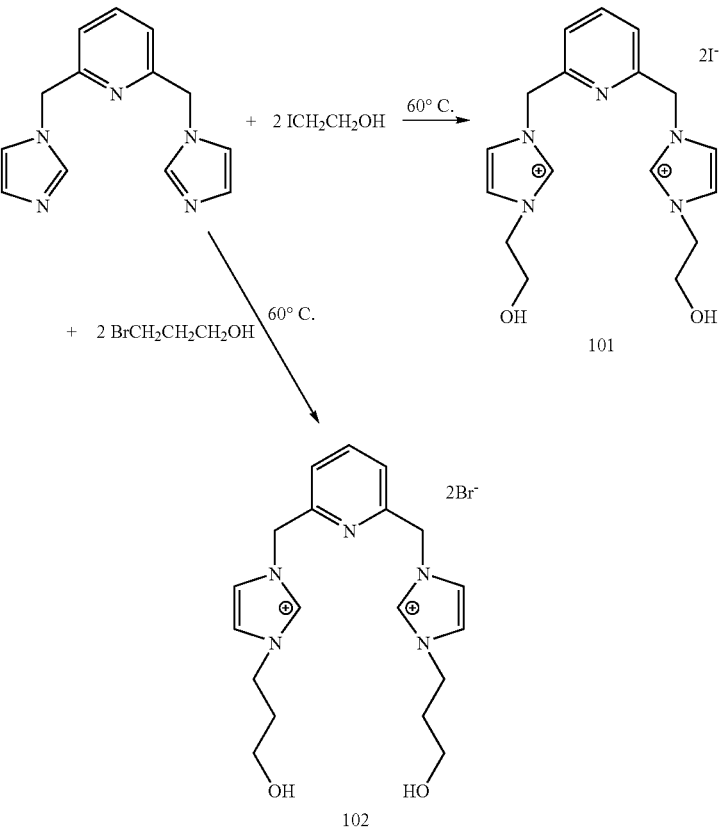

The IR spectra for these compounds show an O—H stretching band vibration, 3325 cm$^{-1}$. FAB-MS spectra obtained from these compounds in nitrobenzyl matrices showed [51][I]$^+$ (C$_{17}$H$_{23}$N$_5$O$_2$I) at m/z 456 and [52][I]$^+$ (C$_{19}$H$_{27}$N$_5$O$_2$Br) at m/z 436. These compounds readily react with Ag$_2$O to form the silver-bis(carbene) pincer complexes 103 and 104 in high yield.

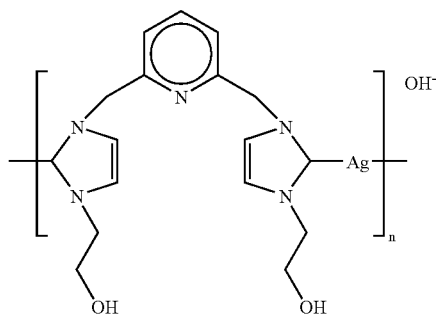

103

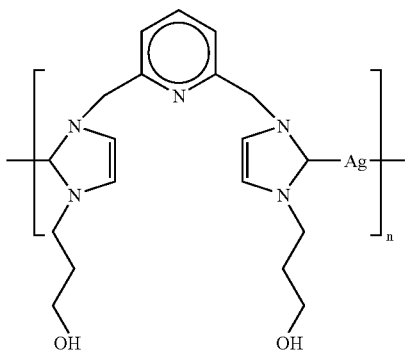

104

The formation of compounds 103 and 104 is confirmed by the loss of the imidazolium proton at 9.13 ppm, 9.36 ppm in the $^1$H NMR spectra of these compounds, and the appearance of a resonance at 181 ppm in the $^{13}$C NMR spectra of these compounds. Further evidence for the formation and structure of compound 103 is provided by X-ray crystallography.

Figure 1B:
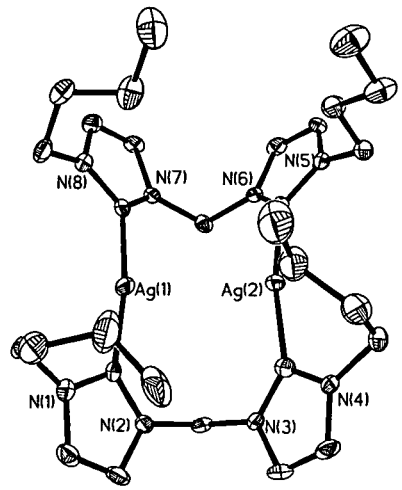
FIG. 1b is a thermal ellipsoid plot of the cationic portions of the water soluble silver dimers shown in formula 9b.

Colorless crystals of compound 103 were obtained by slow evaporation of a methanol solution of compound 103. Interestingly, compound 103 undergoes complete anion exchange in aqueous methanol, replacing the iodide anions with hydroxide anions. In the solid state, compound 103 exists as a one-dimensional linear polymer as shown in FIG. 1. FIG. 1 is a thermal ellipsoid plot of compound 103 with the thermal ellipsoid drawn at a 30 percent probability level. The hydrogen atoms have been omitted from FIG. 1 for clarity.

The geometry at the silver atoms is nearly linear with a C5-Ag1-C15 bond angle of 174.7(4)°, and Ag1-C5, and Ag1-C15 bond distances of 2.108(11) Å and 2.060(13) Å, respectively. Mass spectroscopy suggests that in solution and in the gas phase, compound 103 exists as monomer, whereas X-ray crystallography shows that compound 103 is polymeric in the crystal.

Figure 2:
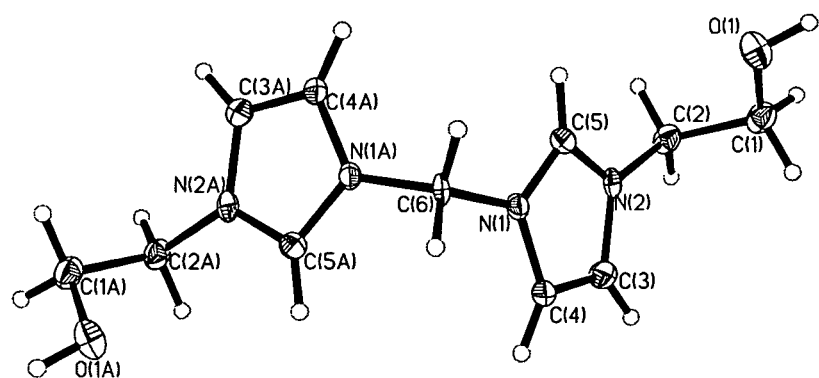
FIG. 2 is a thermal ellipsoid plot of the water soluble diol shown as formula 13.
Figure 3:
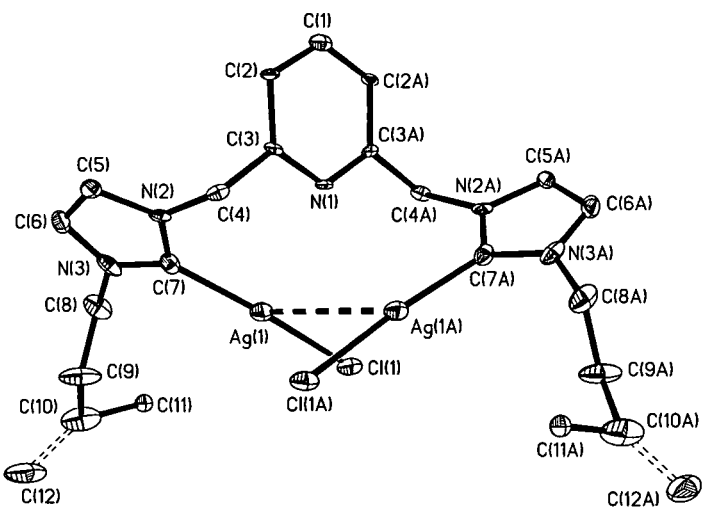
FIG. 3 is a thermal ellipsoid plot of the silver carbine complex shown as formula 17.
Figure 4:
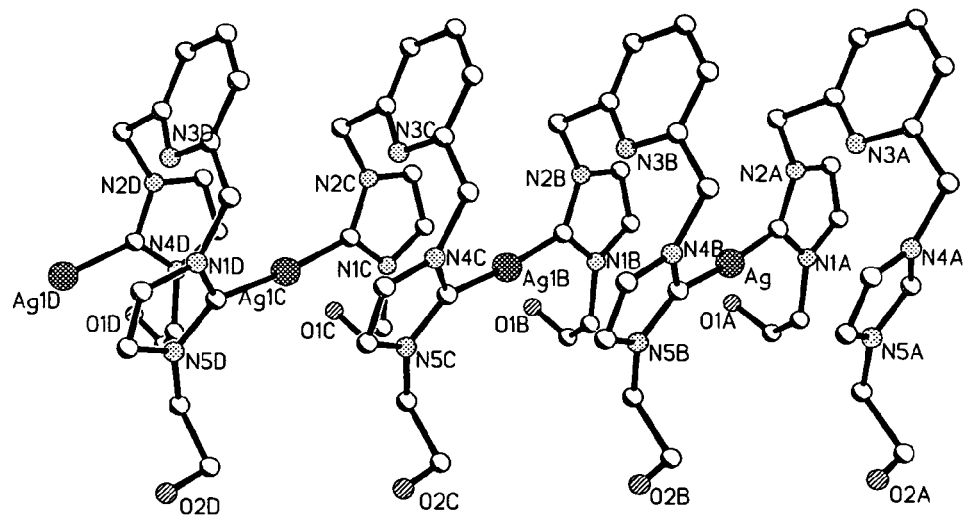

An anion exchange reaction of compound 103 with aqueous ammonium hexafluorophosphate, results in the formation of compound 105. In the solid state, compound 105 exists as a dimer, as shown in FIG. 2. FIG. 2 is a thermal ellipsoid plot of compound 105 with the thermal ellipsoid drawn at a 30 percent probability level. The hydrogen atoms have been omitted from FIG. 2 for clarity. The geometry of the silver atoms are nearly linear with C32-Ag1-C5 (175.7(4)°), C22-Ag2-C17 (174.6(3)°) bonds angles, and Ag1-C32 (2.070(9) Å), Ag1-C5 (2.091(9) Å), Ag2-C22 (2.064(9) Å), Ag2-C17 (2.074(8) Å) bond lengths. The nature of the anions is significant to the structural changes of compound 103 versus compound 105, and the choice of anion has a pronounced effect on the solubility of these compounds. For example, compound 103 is soluble in aqueous media whereas compound 105 is not. Table 1 gives a summary of the crystal data of both of these compounds.

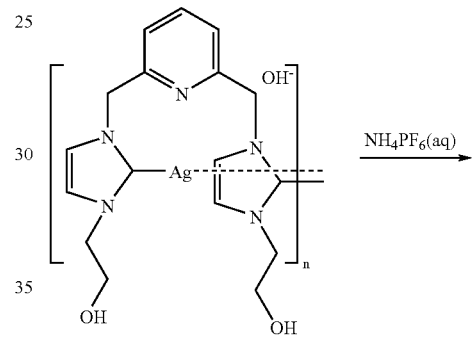

103

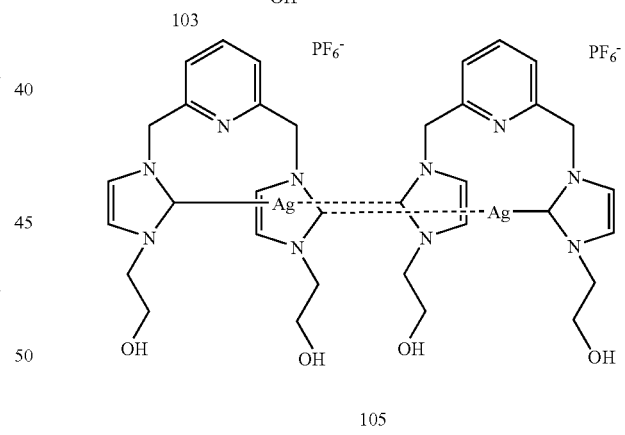

105

TABLE 1

| | 103, C$_{17}$H$_{22}$N$_5$O$_3$Ag | 105, C$_{34}$H$_{42}$N$_{10}$O$_4$AgP$_2$F$_{12}$ |
|---|---|---|
| Empirical Formula | 103, C$_{17}$H$_{22}$N$_5$O$_3$Ag | 105, C$_{34}$H$_{42}$N$_{10}$O$_4$AgP$_2$F$_{12}$ |
| Formula Weight | 434.0735 | 868.1481 |
| Temperature (K) | 100 | 100 |
| Wavelength (Å) | 0.71073 | 0.71073 |
| Crystal system, space group, Z | Orthorhombic, P2(1)2(1)2(1), 4 | Monoclinic, P2(1)/c, 8 |
| Unit cell dimensions | | |
| a (Å) | 4.5586(17) | 10.9448(14) |
| b (Å) | 14.900(6) | 22.885(3) |
| c (Å) | 29.923(12) | 17.729(2) |

TABLE 1-continued

| | | |
|---|---|---|
| α (°) | 90 | 90 |
| β (°) | 90 | 92.196(2) |
| γ (°) | 90 | 90 |
| V (Å$^3$) | 2032.5(14) | 4437.4(10) |
| Dcalc (Mg/m$^3$) | 1.422 | 1.737 |
| Absorption coefficient (mm$^{-1}$) | 1.010 | 1.055 |
| Theta range for data collection (°) | 1.36 to 24.99 | 1.45 to 25.00 |
| Reflections collected/unique | 6300/3506 [R(int) = 0.0650] | 20811/7757 [R(int) = 0.0437] |
| Goodness-of-fit on F$^2$ | 1.034 | 1.058 |
| Final R indices[I > 2 σ (I)] | 0.0655 | 0.0956 |
| R indices (all data) | 0.1410 | 0.2491 |
| Largest difference peak and hole (e Å$^{-3}$) | 0.954 and −0.875 | 2.069 and −1.230 |

The usefulness of compounds 103 and 55 as antimicrobial agents was evaluated. The standard agar plates overlay method was used to obtain the sensitivity data as presented in Table 2. In this test, a filter paper disc of 6 mm diameter was soaked with 20 μL of a silver compound of known concentration, and placed over a lawn of an organism in the agar plate. The diameter of the area in which growth of the organism is inhibited by the test solution was measured after an over night incubation as a measure of the relative antimicrobial activity of the silver compounds. The test organisms were *Escherichia coli, Staphylococcus aureus*, and *Pseudomonas aeruginosa*. Silver nitrate was the reference standard used, while compounds 101 and 102 served as a negative controls.

TABLE 2

Antimicrobial Activity of Silver Compounds

| Tested compounds | Ag+ (μg/ml) | Diameter of Inhibited Area (mm) | | |
|---|---|---|---|---|
| | | E. coli | S. aureus | P. aeruginosa |
| AgNO3 0.5% (w/v) | 3176 | 11.38 | 10.88 | 11 |
| 103 1.31% | 3130 | 11.5 | 11 | 12 |
| 105 1.42% | 3195 | 11.58 | 10.67 | 10.25 |
| 103 0.50% | 1195 | 10.13 | 10 | 11.13 |
| 105 0.50% | 1125 | 10 | 9 | 12 |
| 101 0.50% | | 6 | 6 | 6 |
| 102 0.50% | | 6 | 6 | 6 |

The data confirmed that compounds 103 and 105 have antimicrobial properties at a level comparable to silver nitrate as shown in Table 2. The pincer ligands, compounds 101 and 102, were found to have no antimicrobial activity.

The silver compounds were also tested according to the minimum inhibition concentration determination method (MIC). The MIC is a standard microbiological technique used to evaluate the bacteriostatic activity of antimicrobial agents. In this case, the MIC was based on the total amount of silver available and not on the concentration of silver ions. A 0.5 percent (w/v) solution of each of the silver compounds 103 and 105 was tested. On dissolving of the silver complexes in the culture medium (LB broth), a precipitate of AgCl was observed in all samples. The activity of a dilution series of the supernatant portion of the silver complex solutions was evaluated, with the addition of a constant volume of freshly grown organism (20 μl) per day. *Escherichia coli, Staphylococcus aureus*, and *Pseudomonas aeruginosa* were again used as the test organisms. The MIC was obtained by visual inspection of the cultures for growth(+) or no growth(−) as reported in Table 3. In Table 3, DF is the dilution factor. From the results, it can be concluded that compounds 103 and 105 are less bound to chloride ion than silver nitrate, due to the stability of the Ag—C donor ligand bond. Thus, compounds 103 and 105 show better antimicrobial activity than silver nitrate. This is a desirable property of compounds 103 and 105, when considering silver compounds for in vivo application. It may be noted that although equal weights of silver compounds were used, the amount of silver ions released by compounds 103 and 105 is about 2.7 times lower than the amount of silver ions released by silver nitrate.

TABLE 3

MIC Results of Supernatants of Silver Compounds (less silver chloride)

| Test Ag compounds | Ag (ul/ml) | E. coli | | P. aeruginosa | | S. aureus | |
|---|---|---|---|---|---|---|---|
| | | Day 1 | Day 2 | Day 1 | Day 2 | Day 1 | Day 2 |
| 103 | 1186 | − | − | − | − | − | − |
| ×1DF | | − | + | − | − | − | + |
| ×2DF | | − | + | − | + | + | |
| ×3DF | | + | | + | | + | |
| ×4DF | | + | | + | | + | |
| 105 | 1125 | − | − | − | − | − | − |
| ×1DF | | − | + | − | + | − | + |
| ×2DF | | − | + | − | + | + | |
| ×3DF | | + | | + | | + | |
| ×4DF | | + | | + | | + | |
| AgNO3 | 3176 | − | + | − | + | + | |
| ×1DF | | + | | + | | + | |
| ×2DF | | + | | + | | + | |
| ×3DF | | + | | + | | + | |
| ×4DF | | + | | + | | + | |

While not wishing to condition patentability on any particular theory, it is believed that the activity and stability of compounds 103 and 105, as well as their solubility in water, may be attributed to the relatively slow decomposition of Ag—C donor ligand bond over time to silver metal and silver ion.

When the MIC test was repeated as described above except in the presence of insoluble silver chloride, the activity of the silver compounds was enhanced, with silver nitrate performing better as shown in table 4. It has been previously reported that the presence of chloride contributes to the toxicity of silver in sensitive strains of organisms.

TABLE 4

Effect of chloride (as silver chloride) in the bactericidal activity of the silver compounds

| Tested Ag compounds | E-coli (Days) | | | | | | P. aeruginosa (Days) | | | | | | S. aureus (Days) | | | | | |
|---|---|---|---|---|---|---|---|---|---|---|---|---|---|---|---|---|---|---|
| (% w/v) | 1 | 2 | 3 | 4 | 5 | 6 | 1 | 2 | 3 | 4 | 5 | 6 | 1 | 2 | 3 | 4 | 5 | 6 |
| 103 | | | | | | | | | | | | | | | | | | |
| 0.50 | – | – | – | – | – | – | – | – | – | – | – | – | – | – | – | – | – | – |
| 0.25 | – | – | – | – | – | – | – | – | – | – | – | – | – | – | – | – | – | – |
| 0.12 | – | – | – | – | – | – | – | – | – | – | – | – | – | – | – | – | – | – |
| 0.06 | – | – | – | – | – | – | – | – | – | – | – | – | – | – | – | – | – | – |
| 0.03 | – | – | + | – | – | – | – | – | + | – | – | – | – | + | – | – | – | – |
| 105 | | | | | | | | | | | | | | | | | | |
| 0.50 | – | – | – | – | – | – | – | – | – | – | – | – | – | – | – | – | – | – |
| 0.25 | – | – | – | – | – | – | – | – | – | – | – | – | – | – | – | – | – | – |
| 0.12 | – | – | – | – | – | – | – | – | – | – | – | – | – | – | – | – | – | – |
| 0.06 | – | – | – | – | – | – | – | – | – | – | – | – | – | – | – | – | – | – |
| 0.03 | – | – | + | – | – | – | – | – | + | – | – | – | – | + | – | – | – | – |
| AgNO$_3$ | | | | | | | | | | | | | | | | | | |
| 0.50 | – | – | – | – | – | – | – | – | – | – | – | – | – | – | – | – | – | – |
| 0.25 | – | – | – | – | – | – | – | – | – | – | – | – | – | – | – | – | – | – |
| 0.12 | – | – | – | – | – | – | – | – | – | – | – | – | – | – | – | – | – | – |
| 0.06 | – | – | – | – | – | – | – | – | – | – | – | – | – | – | – | – | – | – |
| 0.03 | – | – | – | + | – | – | – | – | + | – | – | – | – | – | + | – | – | – |

The minimum lethal concentration was determined to evaluate the bactericidal properties of the compounds represented by formulae 103 and 105. The clear (no growth) portion of the culture media with the lowest Ag compound concentration was used, by streaking 0.01 ml of the solution on agar plate using a sterilized loop followed by incubation at 37° C. for 24-48 hours. The colonies were visually counted, with the end point of the minimum bactericidal concentration (MBC) as no growth on the agar plate. The test compounds showed an improved bactericidal effect compared to silver nitrate up to the seventh day of incubation and MBC test, with no growth observed after the tenth day of incubation and testing for the silver compounds. This is despite the fact that freshly grown organisms were added each day to the culture media containing the silver compounds throughout the incubation period. The bactericidal and bacteriostatic properties of 103 and 105 are believed to be due to the slow decomposition of the Ag—C donor (carbene) ligand bond over time to silver metal, silver ion, AgCl and to their solubility in water.

The alkanol N-functionalized silver carbene complexes 103 and 105 are soluble in aqueous media. In addition, they have proved to be useful antimicrobial agents, and their solubility in water makes them excellent silver compounds that can be of use for in vivo application. The solubility and stability of silver complexes in chloride solution have been key factors that have limited the use of silver complexes for in vivo application.

According to another aspect of the present invention, a silver(I) imidazole cyclophane gem diol complex 106 [Ag$_2$C$_{36}$N$_{10}$O$_4$]$^{2+}$2(x)$^-$, where x=OH$^-$, CO$_3$$^{2-}$ was synthesized. The MIC test showed that the antimicrobial activity of the aqueous form of 106 is 2 fold less effective than 0.5% AgNO$_3$, with about the same amount of silver. The antimicrobial activity of 106 was enhanced when encapsulated into Tecophilic® polymer by electrospinning (technique) to obtain mats made of nano-fibers. The fiber mats release aggregates of silver nanoparticles and sustained the antimicrobial activity of the mats over a long period of time. The rate of bactericidal activity of 106 was greatly improved by encapsulation, and the amount of silver used was much reduced. The fiber mat of 106 with 75% (106/tecophilic) contained 2 mg of Ag, which is 8 times lower than 16 mg (0.5%) AgNO$_3$ and 5 times lower than silver sulfadiazine cream 1% (10 mg). The fiber mat was found to kill S. aureus at the same rate as 0.5% AgNO$_3$, with zero colonies on an agar plate and about 6 hours faster than silver sulfadiazine cream. Inoculums tested on and found effective are E. coli, P. aeruginosa, S. aureus, C. albicans, A. niger and S. cerevisiae. Transmission electron microscopy and scanning electron microscopy were used to characterize the fiber mats. The acute toxicity of the ligand (imidazolium cyclophane gem diol dichloride) was assessed by intravenous administration to rats, with an LD 50 of 100 mg/Kg of rat.

An electrospun fiber of the present invention can encapsulate a silver(I) N-heterocyclic carbene complex. The antimicrobial activity of silver(I)-N-pincer 2,6-bis(hydroxylethylimidazolemethyl)pyridine hydroxide, a water soluble silver (I) carbene complex 107, on some clinically important bacteria was described above. Compound 107 is an example of a compound that is sparingly soluble in absolute ethanol but completely soluble in methanol. The solubility of type 1 silver(I) carbene complexes in ethanol, was improved by varying the functionalized groups coupled to the nucleophilic end of the bis(imidazolmethyl)pyridine compound. Although embodiments wherein m=2 and m=3 are shown in forming 107, m can have any positive integer value that is at least 1, and preferably, m has a value within the range of about 1 to about 4. Further, alternate starting materials or precursors described above may be used to produce a desired silver(I) carbene complex without departing from the scope of the present invention. The specific embodiments illustrated and described below are used for illustrative purposes in describing the present invention.

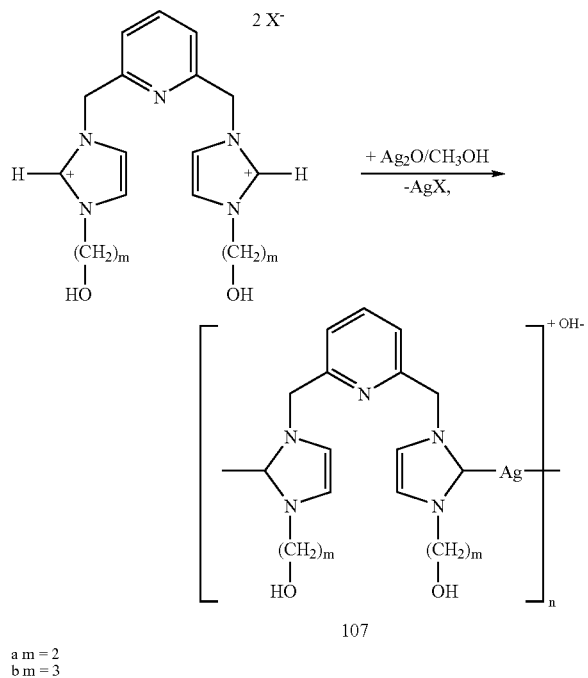

a m = 2
b m = 3

Electrospinning is a versatile method used to produce fibers with diameters ranging from a few nanometers to over microns by creating an electrically charged jet of polymer solution or polymer melt, which elongates and solidifies. The resulting fibers can be used in filters, coating templates, protective clothing, biomedical applications, wound dressing, drug delivery, solar sails, solar cells, catalyst carriers, and reinforcing agents for composites.

The imidazolium (NHC) cyclophane gem-diol salt 108 can be prepared by reacting 2,6-bis(imidazolmethyl)pyridine with 1,3-dichloroacetone as shown below in Eq. 2. The formation of salt 108 as a gem-diol in preference to the carbonyl form is not expected with electron withdrawing groups present. Without being bound to theory, it is believed that the formation of salt 108 as a gem-diol proceeded by acid-catalyzed process with the solution observed to be slightly acidic having a pH range of 5-6.

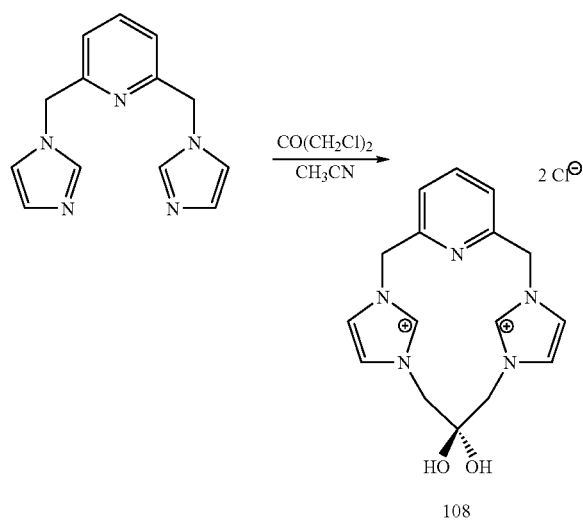

Figure 24:
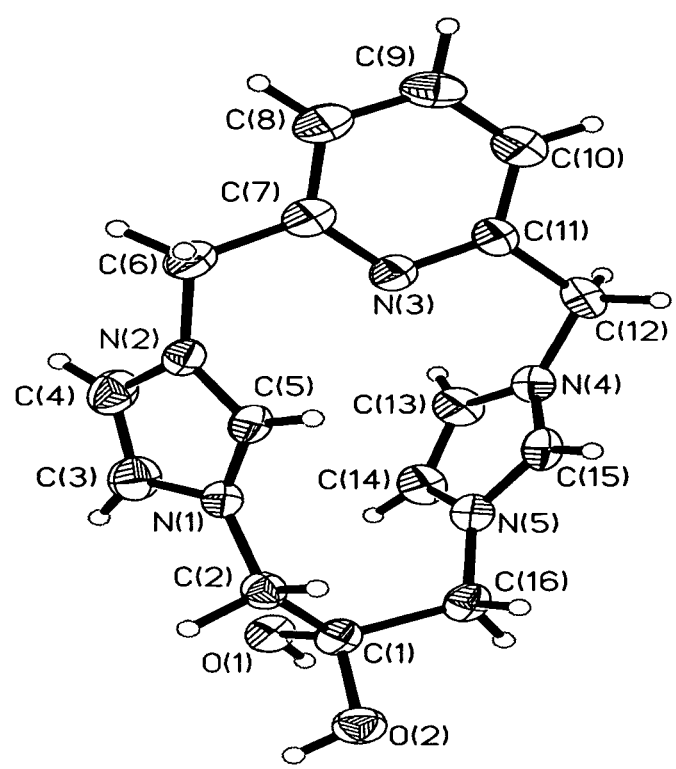
FIG. 24 is a thermal ellipsoid plot of the salt shown in formula 108 with the thermal ellipsoid drawn at 50% probability level. The counter anions are omitted for clarity.

The $^1$H NMR spectra showed the presence of gem O—H as a broad peak at 7.65 ppm, and the absence of C=O in salt 108 was observed in both $^{13}$C NMR and IR spectroscopy. The O—H stretching vibration was observed at 3387 cm$^{-1}$, while the C—O stretching at 1171 cm$^{-1}$ and $^{13}$C NMR chemical shift at 91 ppm. The x-ray crystallography further provided the evidence and structure of 108 as shown in FIG. 24.

The combination of silver(I) oxide with salt 108 in methanol according to the reaction scheme illustrated in Eq. 3 results in complex 106 as an air and light stable yellow solid in high yield, confirmed by the loss of the imidazolium proton at 9.35 ppm of the $^1$H NMR spectra. The proton NMR of complex 106 showed a broad signal with complicated peaks that are not easily assigned. Again, without being bound to theory, this may be due to the fluxional behavior of the compound on the NMR time scale.

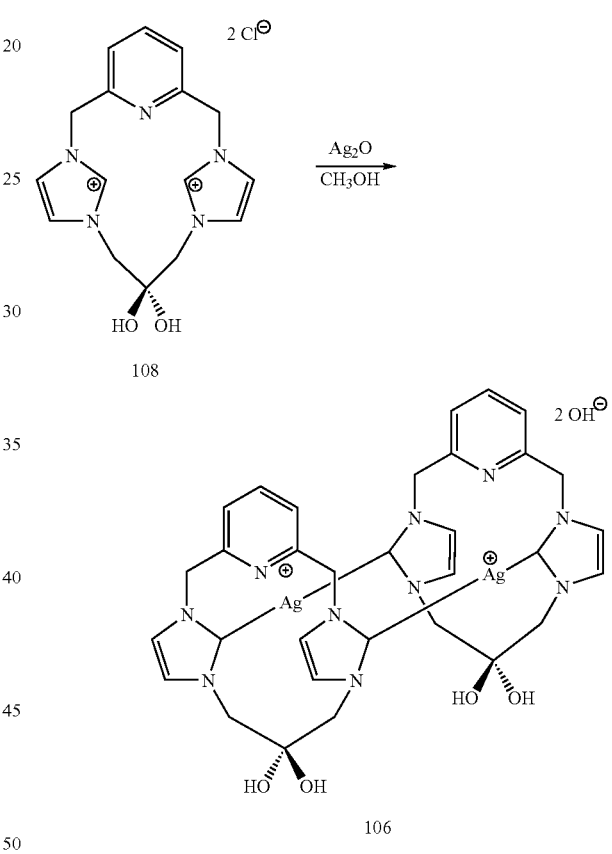

Figure 25:
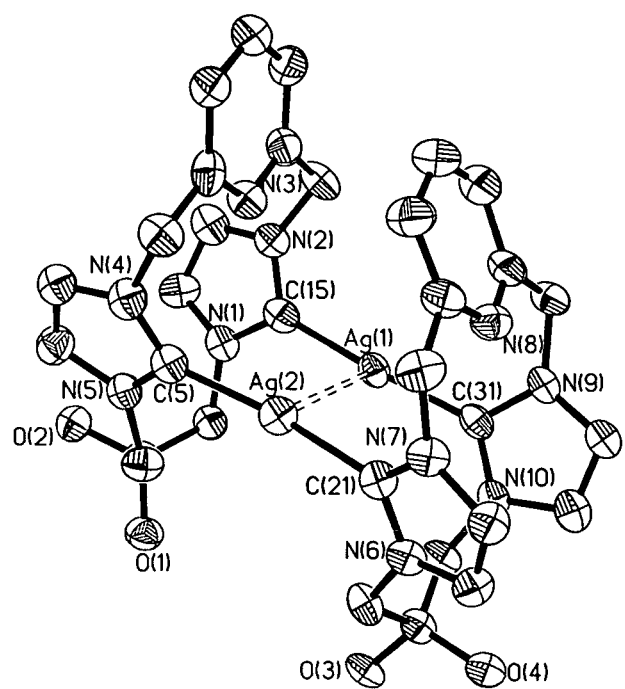
FIG. 25 is a thermal ellipsoid plot of complex 106 with the thermal ellipsoid drawn at 50% probability level. The counter anions are omitted for clarity.

The shift in the resonance signal of the imidazole carbon (NCN) from 138 ppm to downfield of the $^{13}$C NMR spectra at 184 and 186 ppm shows the rare coupling of the Ag—C bond. The large value of the Ag—C coupling constant ($J_{AgC}$=211 Hz) observed agreed with the reported range of 204 Hz-220 Hz for $^{109}$Ag nuclei coupling. $^{109}$Ag coupling is commonly observed due to its higher sensitivity compared to the $^{107}$Ag. The x-ray crystallography confirms the structure of complex 106, which is shown in FIG. 25, with bond distances of Ag1-C15=2.085(5) Å, Ag1-C31=2.077(5) Å, Ag2-C5=2.073(5) Å and Ag2-C21=2.072 Å. A weak Ag1...Ag2 interaction was observed with a bond length of 3.3751(10) Å, longer than the commonly reported Ag—Ag bond range of 2.853-3.290 Å, but shorter than the Van der waals radii for Ag...Ag of 3.44 Å. In silver metal the Ag—Ag bond distance is known to be 2.888 Å. The C—Ag—C bond angles are almost linear with C15-Ag1-C31 bond angle of 175.20(18)° and C21-Ag2-C5 bond angle of 170.56(18)°.

Figure 26A:
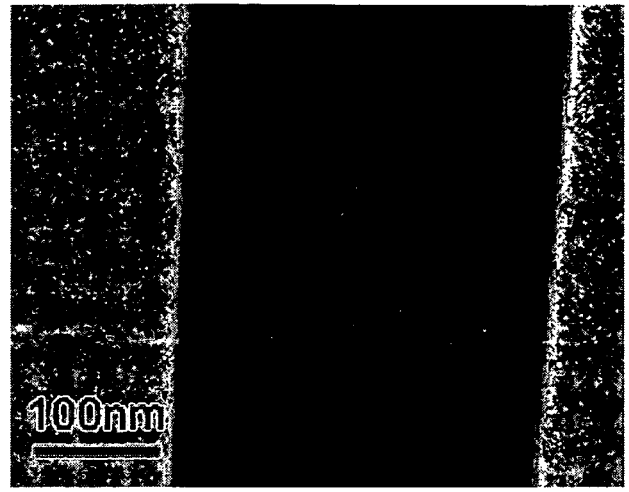
FIGS. 26a and 26b are Electrospun fibers prepared from a mixture of complex 106 and TECOPHILIC® (an aliphatic polyether-based polyurethane) at a weight ratio of 25 to 75.
Figure 26B:
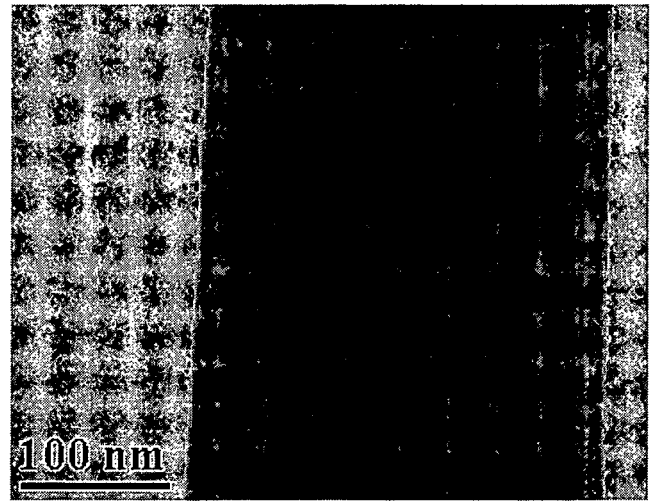
Figure 27A:
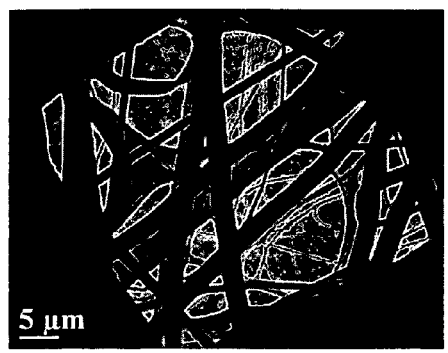
FIGS. 27a and 27b are TEM images showing the release of silver particles by exposing fibers of complex 106 and TECOPHILIC® (an aliphatic polyether-based polyurethane) (weight ratio 50:50) to water vapor environment; 27a details as-spun fiber and 27b details fibers in water vapor environment for 65 hour.
Figure 27B:
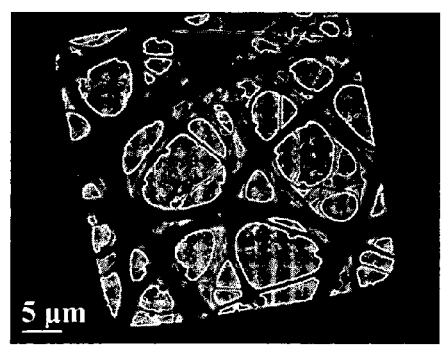

The electrospun fibers from TECOPHILIC® (an aliphatic polyether-based polyurethane) and silver complex were characterized by transmission electron microscopy (TEM) and scanning electron microscopy (SEM). No obvious phase separation was observed in as-spun fibers, shown in FIG. 26, which indicated a generally-uniform mixing of TECOPHILIC® and silver complex. The thickness of the fiber mat was measured by scanning electron microscopy (SEM) with pure TECOPHILIC® (100 micron), 25:75 silver complex 106/TECOPHILIC® (30 microns) and 75:25 complex 106/TECOPHILIC® (60 microns) respectively. The encapsulation of complex 106 by polymer retards the quick decomposition of silver complex into silver ions or particles in an aqueous media. The formation of silver particles at nanometer scale has been observed in the polymer matrix, when the electrospun fiber is exposed to water. Transmission electron microscopy studies showed that the activation of nanosilver particles in the fiber is a process that occurs gradually over a period of time. By exposing the as-spun fibers to water, complex 106 decomposed and release silver ions which aggregated into silver particles at nano-scale measurement. The formation of aggregates of silver particles has been observed within 30 minutes of exposure to water vapor (as shown in FIG. 27). The aggregation of the silver ions in the presence of water, with the aggregate adsorbed on the surface of the fibers is considered to be a simplified mechanism by which the fiber mat releases the active form(s) of the silver for its antimicrobial activity. The fiber of complex 106 is stable in light and air for months, but sensitive to an environment with very high humidity.

Bactericidal Effect

Figures 28A, 28B, 28C:
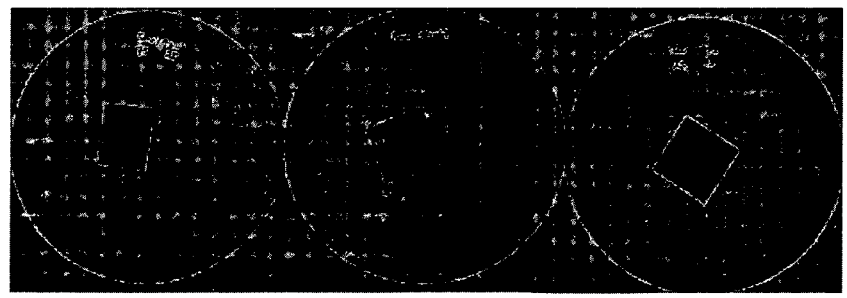
FIGS. 28a, 28b and 28c are images of the susceptibility test of the fiber mat encapsulating complex 106, with bactericidal activity compared to pure TECOPHILIC® (an aliphatic polyether-based polyurethane) fiber mat: (a) Complex 106/TECOPHILIC® (25:75) (b) Pure TECOPHILIC® (c) complex 106/TECOPHILIC® (75:25).

Using a modified Kirby Bauer technique mats of electrospun TECOPHILIC® (an aliphatic polyether-based polyurethane) fiber encapsulating complex 106 and pure electrospun TECOPHILIC® fiber as control were placed on a lawn of organism in an agar plate and incubated overnight at 35° C. The inocula used were both Gram positive and Gram negative prokaryotes (*Escherichia coli, Pseudomonas aeruginosa,* and *Staphylococcus aureus*) of clinical interest. The fungi used were *Candida albicans, Aspergillus niger,* and *Saccharomyces cerevisiae*. The bactericidal activity showed a clear zone of inhibition within and around the fiber mat after an overnight incubation of the agar plate at 35° C. The fungicidal activity was observed after 48 hrs of incubation at 25° C. Pure TECOPHILIC® fiber mat as control showed no growth inhibition (See FIG. 28). No obvious difference was observed in the diameter of the cleared zone of inhibition around the fiber mat when the composition of the fiber mat was changed from 75% of complex 106 and 25% TECOPHILIC® to 25% of complex 106 and 75% TECOPHILIC®. The diameter of the zone of inhibition for the 75% (complex 106/TECOPHILIC®) fiber mat is 4.00 mm while that of 25% (complex 106/TECOPHILIC®) is 2.00 mm. The difference in diameter of the zone of inhibition between the two types of fiber mat has no linear relationship with the amount of silver (3:1 ratio) present in the two fiber mats. These result further shows the limitation of the Kirby Bauer technique as a quantitative tool to determine the antimicrobial activity of drugs. The diffusing ability of the silver ions might have been limited by the formation of secondary silver compounds. Ionic silver is known to undergo ligand exchange reactions with biological ligands such as nucleic acids, proteins, and cell membranes.

Figure 29:
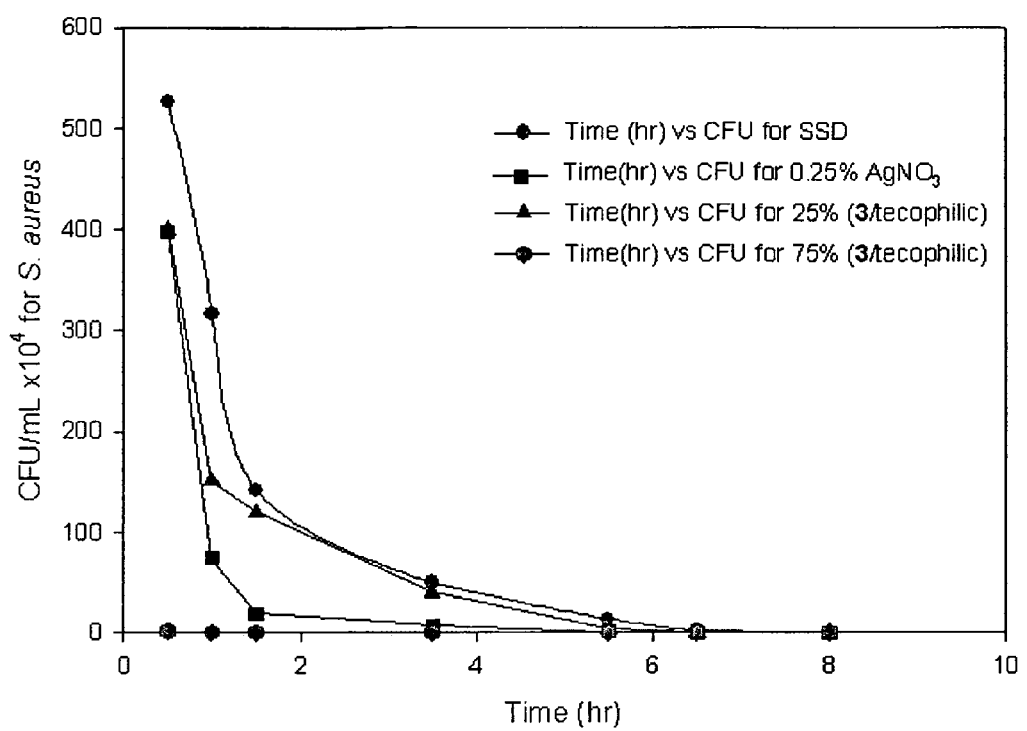
FIG. 29 is a graph showing CFU (colony forming unit) versus Time (hours) of the silver compounds on S. aureus, expresses the kinetic of the bactericidal activity for each of the silver compounds tested.

Deposition of a few silver particles was observed at the bottom of a test tube when a piece of the fiber mat was placed in 5 mL of distilled water and exposed to light for 4 days. The leaching of the silver particles from the fiber mat surfaces to the solution occurred gradually over time. The release of nano-silver particles from the as-spun mats of complex 106 into an aqueous medium lead to the investigation of the kinetics of kill (bactericidal activity) of the as-spun fiber mat of complex 106 with respect to time by comparing it with silver nitrate and silver sulfadiazine 1% cream or silvadene (SSD), a clinical drug widely in use. Both types of the fiber mat composition 75:25 (amount of Ag=424 µg/mL) and 25:75 (amount of Ag=140 µg/mL) used in this study showed a faster kill rate than SSD (amount of Ag=3020 µg/mL). Silver nitrate (0.5%) with 3176 µg/mL of Ag showed about the same kill rate as complex 106/TECOPHILIC® 75:25 (Ag=424 µg/mL) at a silver concentration 8 fold lower than silver nitrate (see FIG. 29). Bactericidal activity of the silver compounds is faster on *P. aeruginosa* than on *S. aureus*. The fiber mats killed bacteria faster and better than silvadene.

The time dependence of the bacteriostatic and bactericidal activities of the as-spun mat of complex 106 as a function of the volume of organism inoculated was examined. The fiber mats of complex 106 showed an effective bactericidal activity on *P. aeruginosa, E. coli* and *S. aureus* for over a week with daily inoculation (25 µL) of freshly grown organism. This is an indication that the as-spun fiber mat sustained the continuous release of active silver species over a long period of time. Pure TECOPHILIC® (an aliphatic polyether-based polyurethane) mat as control showed no antimicrobial activity within 24 hrs of incubation. The as-spun mat of complex 106 with the 75% complex 106/TECOPHILIC® composition showed better bactericidal effect on *P. aeruginosa* than the 25% complex 106/TECOPHILIC® for over 2 weeks after inoculating with over 200 µL ($2\times10^7$) of freshly grown organism. Bacteriostatic activity was observed for *S. aureus* and *E. coli* after 10 days of the daily streaking of the LB broth solution on an agar plate. Visual inspection of the incubated solutions showed no growth of the organism.

The bactericidal activity of 108, complex 106 and $AgNO_3$ in aqueous LB broth was studied using the minimum inhibitory concentration (MIC) test. There was generally no difference in the bactericidal activity and MIC of complex 106 and $AgNO_3$ after 24 hrs of incubation as shown in Table 5. However, after 48 hrs of incubation, silver nitrate showed a better antimicrobial activity at a concentration 2 fold lower than complex 106 (838 µg/mL).

MIC Result Comparing the Activity of $AgNO_3$ and 106, with Both Having About the Same Amount of Silver.

TABLE 5

MIC result comparing the activity of $AgNO_3$ and complex 106, with both having about the same amount of silver.

| Sample ID | Conc. of sample (wt/V %) | Conc. of sample (µg/mL) | Vol. of bacteria (µL) | E. coli (Day) | | P. aereginousa (Day) | | S. aureus (Day) | |
|---|---|---|---|---|---|---|---|---|---|
| | | | | 1 | 2 | 1 | 2 | 1 | 2 |
| $AgNO_3$ | 0.50 | 3462.35 | 100 | − | − | − | − | − | − |
| | 1DF | 1731.18 | | − | − | − | − | − | − |
| | 2DF | 865.59 | | − | − | − | − | − | − |
| | 3DF | 432.79 | | − | − | − | − | − | − |
| | 4DF | 216.40 | | − | + | − | − | − | + |

TABLE 5-continued

MIC result comparing the activity of AgNO₃ and complex 106, with both having about the same amount of silver.

| Sample ID | Conc. of sample (wt/V %) | Conc. of sample (µg/mL) | Vol. of bacteria (µL) | E. coli (Day) 1 | E. coli (Day) 2 | P. aereginousa (Day) 1 | P. aereginousa (Day) 2 | S. aureus (Day) 1 | S. aureus (Day) 2 |
|---|---|---|---|---|---|---|---|---|---|
| 106 | 1.38 | 3341.48 | 100 | − | − | − | − | − | − |
|  | 1DF | 1675.74 |  | − | − | − | − | − | − |
|  | 2DF | 837.87 |  | − | − | − | − | − | − |
|  | 3DF | 418.94 |  | − | + | − | + | − | + |
|  | 4DF | 209.47 |  | − | + | − | + | − | + |
| 108 | 0.5 |  | 25 | + |  | + |  | + |  |

DF is the dilution factor (1 mL).
+ = growth,
− = no growth.
The amount of silver (µg) per mL for each compound was calculated as (molecular mass of Ag/formula wt of compound) × wt %.

The MIC value was not determined for silver sulfadiazine because of the cloudy nature of the solution, and the concentration of 108 used showed no antimicrobial activity. The dilutions with the least concentration of complex 106 (209 µg/mL) and AgNO₃ (216 µg/mL) in the MIC test was observed to show growth of the same number of colonies of S. aureus on an agar plate after 24 hrs of incubation. The 25% complex 106/TECOPHILIC® (an aliphatic polyether-based polyurethane) fiber mat has the least concentration of Ag, 140 µg/mL (see Table 6), and sustain the release of active silver species that were bio-available for days. No growth of the organism was observed with the daily increase in the volume of inocula.

TABLE 6

Showing details of silver compounds used for the kinetic studies.

| Sample ID | Wt of Ag compds. used (mg) | Volume of LB Broth (ml) | Amount of Ag in sample (mg) | µg of Ag/ml |
|---|---|---|---|---|
| SSD | 20.00 | 5.00 | 6.05 | 1210.00 |
| AgNO₃ | 12.80 | 5.00 | 8.13 | 1626.00 |
| AgNO₃ | 25.00 | 5.00 | 15.90 | 3176.00 |
| 106/Tecophilic (25:75) | 11.30 | 5.00 | 0.73 | 146.00 |
| 106/Tecophilic (75:25) | 11.40 | 5.00 | 2.21 | 441.00 |

SSD: silver sulfadiazine 1% cream

Thus, the antimicrobial activity of complex 106 was enhanced for a longer period, at a very low concentration of Ag particles by encapsulation in a suitable polymeric fiber. The bactericidal activity of the fiber mat 75% (complex 106/TECOPHILIC® (an aliphatic polyether-based polyurethane)) with 424 µg/mL of silver is 8 fold lower in the concentration of Ag than AgNO₃ (3176 µg/mL) and showed not only a kill rate as fast as silver nitrate, but also retained the original color of the LB broth, a clear yellow solution unlike silver nitrate which stains and changed the LB broth color to dark brown. The silver-sulfadiazine cream did not readily dissolve in the aqueous LB broth, thus affecting the rate of its bactericidal activity.

Figures 30A, 30B:
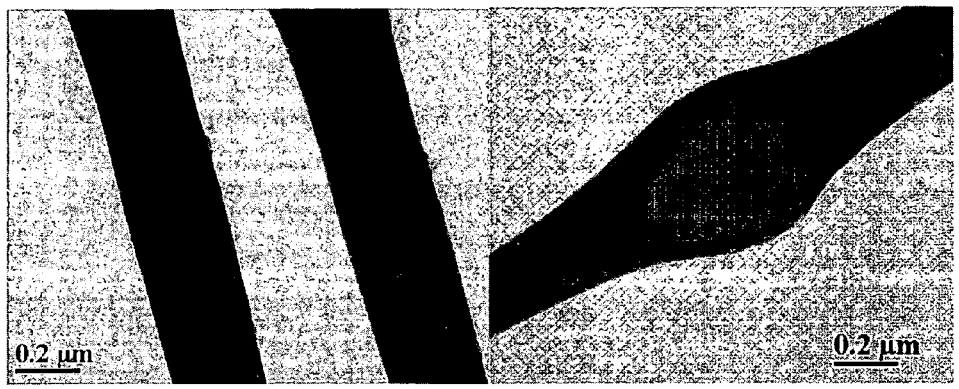
FIGS. 30a, 30b, 30c and 30d are images of Electrospun fibers from complex 106 and TECOPHILIC® (an aliphatic polyether-based polyurethane) (75:25) after two weeks of antimicrobial activity in LB broth media: (a) Stereo images of a segment of fiber; (b) A large aggregate (400 nm) of silver particles encapsulated in TECOPHILIC® fiber (c) Silver aggregates (200 nm to 300 nm in diameter) and silver particles (10 nm to 20 nm in diameter) in TECOPHILIC® matrix; (d) Top view of the fiber mat with aggregates of silver particles.
Figures 30C, 30D:
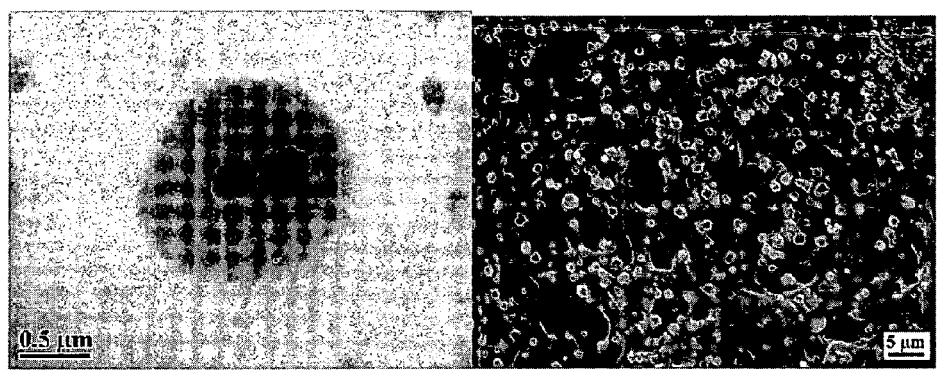

The antimicrobial activity of the fiber mat encapsulating complex 106 can be considered to be a combination of active silver species, which may include $AgCl_2^-$ ions, clusters of $Ag^+$ ions, AgCl and free $Ag^+$ ions. Theoretically, the slow release of the active silver particles in the solution leads to the quick formation of silver chloride. The presence of more chloride anion as the major counter ion will further result in the formation of negatively charged $[Ag_yCl_x]^{n-}$ ion species (where y=1, 2, 3 . . . etc; x=2, 3 . . . (y+1); n=x−1). The anionic silver complexes of the type $[AgI_3]^{2-}$, $[Ag_2I_4]^{2-}$, $[Ag_4I_8]^{4-}$ and $[Ag_4I_6]^{2-}$ have been formed. The formation of anionic silver chloride species may not be limited to the leached aggregates of silver particles in the solution, but may also be found on the surface of the fiber mats as shown in the SEM images of FIG. 30. Anionic silver dichloride is known to be soluble in an aqueous media and thus will be bio-available. It has been reported that anionic silver halides are toxic to both sensitive and resistance strain bacteria. The adsorbed active silver species on the network of fibers in the mat is an advantage the fiber mat has to increase the surface area of the active silver species over the conventional use of aqueous silver ions. This mechanism might have accounted for the effective bactericidal activity of the fiber mat in an aqueous media, even at such a low concentration of silver compared to the un-encapsulated form of complex 106. Although complex 106 is sparingly soluble in water, its quick decomposition has been observed to occur in aqueous media. Thus, the bactericidal activity of complex 106 is reduced due to poor availability of active silver species in the LB broth media, which might be due to the formation of secondary silver compound especially AgCl.

Acute Toxicity Assessment

The LD 50 assessment was done by intravenous administration of 108, dissolved in a buffered saline solution, via the tail of rats. Adult rats were used with an average weight of 500 g. Progressive administration of 0.3 ml of the dose (5 mg, 50 mg) was done weekly. The rats were carefully examined for the dose-response effect. Death occurred 10 minutes after administrating 50 mg of 108, when 50% of the rats showed powerful convulsion before death. Autopsy report showed pulmonary hemorrhage and hemorrhage in the brain of the dead rats, a diagnosis of stroke. The surviving rats were observed to lose weight, with a drastic loss in appetite, and low urine out put. The LD 50 assessment was found to be 100 mg/Kg of rat.

The synthesis of 108 with functionalized groups aids in tailoring the encapsulation of the silver(I) imidazole cyclophane gem diol into a nanofiber. The fiber mat has been shown to have improved the antimicrobial activity of the silver(I)-n-heterocyclic carbene complexes on the inoculum, with a faster kill rate than silvadene in an LB broth medium at a concentration 8 fold lower than silvadene. The encapsulation of the silver N-heterocyclic carbene complexes increases the bio-availability of active silver species and also reduces the amount of silver used. Encapsulated silver(I) carbene complexes in nano-fibers has been demonstrated to be a promising material for sustained and effective delivery of silver ions over a longer period of time with maximum bactericidal activity than supplying silver in an aqueous form. The amount of silver required for antimicrobial activity is reduced with this technique of encapsulation compared to the un-encapsulated form, which often is related to the amount of silver in 0.5% silver nitrate. Furthermore, the ability of the fiber mat to retain the original color of the LB broth is a major cosmetic plus. The assessment of the acute toxicity of the ligand on rats showed an LD50 of 100 mg/Kg of rat, a value considered to be moderately toxic.

In addition to useful antimicrobial, or antibacterial, properties, it is believed that the present invention can inhibit fungal growth, and also viral growth. The compositions of matter and methods of the present invention also contemplate delivery of Silver to locations via any known vehicle, including, but not limited to, inhalation through the lungs, direct application of a liquid to an eye, and direct application to a urinary bladder infection, or any other type of topical application.

General Experimental

Silver (I) oxide, silver sulfadiazine and 1,3-dichloroacetone where purchased from Aldrich. Acetone, acetonitrile, methanol, ethanol, ammonium hexafluorophosphate, and organisms; S. cerevisiae (ATCC 2601), C. albicans (ATCC 10231), A. niger (ATCC 16404), E. coli (ATCC 8739), P. aeruginosa (ATCC 9027), S. aureus (ATCC 6538) were purchased from Fisher. All reagents were used without further purification. Infrared spectra were recorded on Nicolet Nexus 870 FT-IR spectrometer. The $^1$H and $^{13}$C NMR data was recorded on a Varian Gemini 300 MHz instrument, and the spectra obtained were referenced to the deuterated solvents. Mass spectroscopy data were recorded on an ESI-QIT Esquire-LC with a positive ion polarity. The TEM images were recorded on FEI TE CNAI-12 transmission electron microscope (TEM) at 120 KV.

Synthesis of the Imidazolium Cyclophane Gem-Diol Dichloride

A solution containing 0.24 g (1.0 mmol) of 2,6-bis(imidazolemethyl)pyridine and 0.254 g (2.0 mmol) 1,3-dichloroacetone in 60 ml of acetonitrile was stirred at 75° C. for 8 h to obtain 108 as a brown solid on filtration. Yield: 0.9 mmol, 89.6%. Colorless crystals of the $PF_6$ salt of 108 were obtained by slow evaporation from acetonitrile/water. Mp: 175-178° C. $^1$H NMR (300 MHz, DMSO-$d_6$): δ4.68 (s, 4H, $CH_2C$ $(OH)_2CH_2$), 5.67 (s, 4H, $CH_2$), 7.40, (s, 2 H, NC(H)CH), 7.47 d, 2H, J=7.8 Hz, m-pyr), 7.65 (s, 2H, $C(OH)_2$), 7.89 (s, 2H, NCHC(H)), 7.94 (t, 1H, J=7.8 Hz, p-pyr), 9.34 (s, 2H, NC(H) N). $^{13}$C NMR (75 MHz, DMSO-$d_6$): δ51.8, 55.2, 91.1, 120.5, 122.0, 123.9, 138.0, 138.8, 152.6. ESI-MS m/z: 384 [$M^2$+ 2Cl$^-$], 348 [$M^{2+}$Cl$^-$]. FT IR (Nujol, cm$^{-1}$): 3387, 3105, 1597, 1564, 1439, 1346, 1171, 1085, 996, 755. Anal. Calcd: C, 48.54; H, 4.41; N, 16.94; Cl, 17.13. Found: C, 48.33; H, 4.32; N, 16.71; Cl, 16.76.

Synthesis of the Dinuclear Silver Carbene Cyclophane Gem-Diol Hydroxide

The combination of 0.232 g (1.0 mmol) silver(I)oxide and 0.366 g (0.9 mmol) of 108 in 70 ml methanol was stirred at room temperature for 50 minutes. The filtrate was concentrated to obtain complex 106 as a yellow solid. Single crystals of complex 106 were obtained from ethanol, containing a spike of carbonate, by slow diffusion.

Yield: 0.618 g, 0.738 mmol, 82%. Mp: 202-204° C. ESI-MS m/z: 400[0.5$M^{2+}$], 801[$2M^+$], 837[$2M^+2OH^-$]. FTIR (Nujol, cm$^{-1}$): 3415, 3105, 1596, 1564, 1439, 1344, 1169, 1084, 1028, 996, 758. $^{13}$C NMR (75 MHz, DMSO-$d_6$): δ48.6, 51.1, 53.8, 92.1, 119.9 (J=1.4 Hz), 121.6, 128.6, 137.8 (J=2.4 Hz), 154.2, 184.9 (Jcarbene-Ag=211 Hz). Anal. Calcd: Ag, 24.54; C, 43.79; H, 4.20; N, 15.24. Found: C, 43.15; H, 4.22; N, 14.89.

Electrospun Fiber

TECOPHILIC® (an aliphatic polyether-based polyurethane) was dissolved in a mixture of ethanol and tetrahydrofuran at a ratio of 9 to 1. A solution of complex 106 in ethanol was mixed with a pre-made solution of TECOPHILIC®. Solutions with different weight ratios between complex 106 and TECOPHILIC® were prepared. The ratios were 0/100, 25/75 and 75/25. The solutions of complex 106 and TECOPHILIC® were held in a pipette. An electrical potential difference of 15 KV was applied between the surfaces of the solution drop to the grounded collector, a distance of about 20 cm. Transmission electron microscopy (TEM) and scanning electron microscopy (SEM) were used to characterize the as-spun fibers and fibers exposed to water.

Antimicrobial Test

Sterilized LB Broth was measured (5 mL) into a sterile tube. A loopful of stationary phase cultured microorganism (E. coli, P. aeruginosa, S. aureus) was introduced into the tube containing the LB Broth solution. The mixture was cultured overnight, at 35° C. in a shaking incubator. The same procedure was done with stationary phased cultured fungi (C. albican, S. cerevisae, A. niger) and incubated without shaking at room temperature for 72 hrs.

Fiber Mat Testing

A constant volume (25 μL) of the freshly grown organism was placed on an LB agar plate and grown to obtain a lawn of the organism. A fiber mat (2.0 cm×2.0 cm) of complex 106 and pure TECOPHILIC® (an aliphatic polyether-based polyurethane) was placed on a lawn of bacteria (E. coli, P. aeruginosa, S. aureus) of an LB agar plate and incubated overnight at 35° C. The bactericidal activity was observed by visual inspection of growth and no growth in and around the area of the fiber mat. About the same dimension of the fiber mat was placed on a lawn of fungi (C. albicans, S. cerevisiae, A. niger) and incubated at room temperature for 48 hrs. The diameter of the clear zone was measured.

Minimum Inhibitory Concentration (MIC) Test

Serial dilutions were made to obtain a range of concentrations by transferring 1 mL of freshly prepared stock solution of the silver compounds (with the same amount of silver particles) into a sterile culture tube containing 2 mL of LB broth, marked A. 1 mL of well mixed solution of A was transferred to culture tube B containing LB broth. The same procedure was repeated to obtain the dilute solution for tube C, D and E. The MIC was determined by visual inspection of growth/no-growth of the above concentrations of the silver compounds marked A-E inoculated with 25 μL of the organisms. After incubation at 35° C. overnight with no growth of organism, an additional 80 μL of freshly grown organisms was added to each of the culture on the second day and incubated at the same temperature.

Kinetic Test of Bactericidal Activity

Equal volume (5 mL) of LB broth were measured into sterile culture tubes and inoculated with 100 μL of S. aureus to each tube containing silver nitrate (12.8 mg, 25 mg), silver sulfadiazine (20 mg), 11.3 mg complex 106/TECOPHILIC® (an aliphatic polyether-based polyurethane) (25:75) and 11.4 mg complex 106/TECOPHILIC® (75:25) fiber mats. The mixtures were incubated at 35° C. and the bactericidal activity was checked over a range of time by streaking one loopful of each mixture on an agar plate. The agar plate was then incubated at 37° C. overnight and the numbers of colonies of organism formed counted. The same procedure was repeated using 100 μL P. aeruginosa.

Animal Studies

Male Sprague Dawley available from Harlan Sprague Dawley (Indianapolis, Ind.) adult rats (400-500 g body weight) were housed in the university of Akron animal facility. Temperature and humidity were held constant, and the light/dark cycle was 6.00 am-6.00 pm: light, 6.00 pm-6.00 am: dark. Food available from Lab diet 5P00, Prolab, PMI nutrition, Intl. (Bretwood, Mo.) and water were provided ad libitum. Animals were anesthetized with ether in order to inject the compound into the tail vein, using a 27 gauge syringe needle in a volume of 0.3 ml sterile saline. The dosages for the ligand were 5 mg and 50 mg. At the end dosages of the experiment, animals were terminated and the liver, lung, kidney and heart tissues were removed and frozen at −70° C. Urine samples were collected daily for later examination of the compound distribution. These studies were approved by the University of Akron Institutional Animal Care and Use Committee (IACUC).

X-Ray Crystallographic Structure Determination

Crystal data and structure refinement parameters contained in the supporting information. Crystals of 108 and complex 106 were each coated in paraffin oil, mounted on kyro loop, and placed on a goniometer under a stream of nitrogen. X-ray data were collected at a temperature of 100 K on a Brucker Apex CCD diffractometer using Mo Kα radiation ($\lambda=0.71073$ Å). Intensity data were integrated using SAINT software, and an empirical absorption correction was applied using SADABS. Structures 108 and complex 106 were solved by direct methods and refined using full-matrix least square procedures. All non-hydrogen atoms were refined with anisotropic displacement.

It should be evident that the present invention is highly effective in providing a method of inhibiting microbial growth by administration of a N-functionalized silver carbene complex. It is, therefore, to be understood that any variations evident fall within the scope of the claimed invention and thus, the selection of specific component elements can be determined without departing from the spirit of the invention herein disclosed and described.

We claim:

1. A silver complex of an N-heterocyclic carbene represented by any one of the formulas:

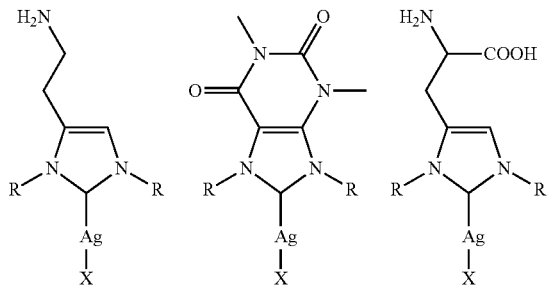

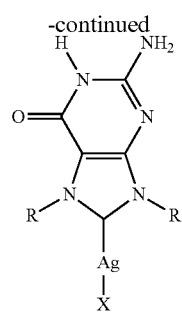

where each R is independently selected from a hydrogen, a C1 to C12 alkyl, a C1 to C12 substituted alkyl, a C1 to C12 alkoxy, a C3 to C12 cycloalkyl, a C3 to C12 substituted cycloalkyl, a C2 to C12 alkenyl, a C3 to C12 cycloalkenyl, a C3 to C12 substituted cycloalkenyl, a C2 to C12 alkynyl, a C5 to C12 aryl, a C5 to C12 substituted aryl, a C1 to C12 alkylamine, a C1 to C12 substituted alkylamine, a C1 to C12 alkylpentose phosphate, a phenol, a C1 to C12 ester, or a C5 to C12 alkylaryl, and where X is selected from a halide, a carbonate group, an acetate group, a phosphate group, a hexafluorophosphate group, a tetrafluoroborate group, a nitrate group, a methylsulfate group, a hydroxide or sulfate.

2. The silver complex of claim 1, wherein the silver complex is represented by the following formula:

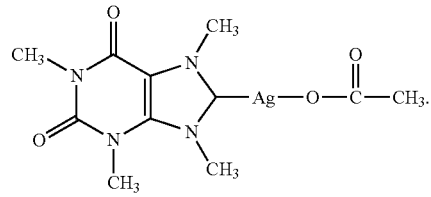

* * * * *